US009201004B2

(12) United States Patent
Sakagawa

(10) Patent No.: US 9,201,004 B2
(45) Date of Patent: Dec. 1, 2015

(54) IMAGE PROCESSING APPARATUS, OCT IMAGING APPARATUS, TOMOGRAPHIC IMAGING SYSTEM, CONTROL METHOD, AND PROGRAM

(75) Inventor: Yukio Sakagawa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 350 days.

(21) Appl. No.: 13/634,342

(22) PCT Filed: Mar. 25, 2011

(86) PCT No.: PCT/JP2011/001765
§ 371 (c)(1),
(2), (4) Date: Sep. 12, 2012

(87) PCT Pub. No.: WO2011/121959
PCT Pub. Date: Oct. 6, 2011

(65) Prior Publication Data
US 2013/0002711 A1 Jan. 3, 2013

(30) Foreign Application Priority Data

Mar. 31, 2010 (JP) .................................. 2010-082811
Feb. 17, 2011 (JP) .................................. 2011-032218

(51) Int. Cl.
*G01N 21/47* (2006.01)
*A61B 3/00* (2006.01)
(Continued)

(52) U.S. Cl.
CPC .......... *G01N 21/4795* (2013.01); *A61B 3/0025* (2013.01); *A61B 3/102* (2013.01);
(Continued)

(58) Field of Classification Search
CPC ......... G06T 17/00; G06T 17/20; G06T 19/00;
G06T 15/00; G06T 15/005; A61B 3/02;
A61B 3/1015; A61B 3/103; A61B 3/12;
A61B 3/1225; A61B 3/14
USPC ......... 702/155, 156, 157, 158, 166, 167, 170,
702/172; 351/200, 205, 206, 221; 345/418,
345/419, 420, 619
See application file for complete search history.

(56) References Cited

U.S. PATENT DOCUMENTS

2007/0046948 A1* 3/2007 Podoleanu et al. ........... 356/497
2007/0070295 A1 3/2007 Tsukada et al.
(Continued)

FOREIGN PATENT DOCUMENTS

CN 001659503 A 8/2005
CN 001924633 A 3/2007
(Continued)

*Primary Examiner* — James A Thompson
(74) *Attorney, Agent, or Firm* — Canon USA Inc. IP Division

(57) ABSTRACT

An image processing apparatus capable of acquiring OCT tomographic images that can be captured by an OCT imaging apparatus configured to scan a target to be captured with low-coherence light along a predetermined main scanning line. The image processing apparatus includes an image acquisition unit configured to acquire a plurality of OCT tomographic images of the target to be captured along a plurality of main scanning lines that are different in direction, and a display control unit configured to display the plurality of OCT tomographic images on a display screen using a layout that can express differences in the direction of each main scanning line so as to reflect a relative relationship between respective main scanning line directions with respect to the target to be captured in respective OCT tomographic images.

21 Claims, 17 Drawing Sheets

(51) Int. Cl.
  *A61B 3/10* (2006.01)
  *G01B 9/02* (2006.01)
  *A61B 5/00* (2006.01)

(52) U.S. Cl.
  CPC ......... *G01B 9/0203* (2013.01); *G01B 9/02007* (2013.01); *G01B 9/02019* (2013.01); *G01B 9/02027* (2013.01); *G01B 9/02089* (2013.01); *G01B 9/02091* (2013.01); *A61B 5/0066* (2013.01)

(56) References Cited

U.S. PATENT DOCUMENTS

| | | | |
|---|---|---|---|
| 2008/0100612 A1* | 5/2008 | Dastmalchi et al. | 345/418 |
| 2008/0208525 A1 | 8/2008 | Kikawa et al. | |
| 2009/0257636 A1 | 10/2009 | Wei et al. | |
| 2011/0032479 A1 | 2/2011 | Utsunomiya | |
| 2011/0134436 A1* | 6/2011 | Podoleanu et al. | 356/512 |

FOREIGN PATENT DOCUMENTS

| | | |
|---|---|---|
| CN | 001939208 A | 4/2007 |
| CN | 101084824 A | 12/2007 |
| CN | 101251365 A | 8/2008 |
| CN | 101563017 A | 10/2009 |
| EP | 1908397 A2 | 4/2008 |
| JP | H06-511312 A | 12/1994 |
| JP | 2007-130403 A | 5/2007 |
| JP | 2007117714 A | 5/2007 |
| JP | 2008-154939 A | 7/2008 |
| JP | 2008209166 A | 9/2008 |
| WO | 2011007657 A1 | 1/2011 |

* cited by examiner

IMAGE PROCESSING APPARATUS, OCT IMAGING APPARATUS, TOMOGRAPHIC IMAGING SYSTEM, CONTROL METHOD, AND PROGRAM

TECHNICAL FIELD

The present invention relates to an image processing apparatus that displays a tomographic image, an optical coherence tomography (OCT) imaging apparatus, a tomographic imaging system, a control method, and a computer program.

BACKGROUND ART

An optical coherence tomography (OCT) imaging apparatus can obtain a tomographic image that visualizes an internal structure of a target to be captured based on the principle of optical coherence tomography (OCT). The OCT imaging apparatus enables an eye doctor or any other specialist to diagnose the stage of a disease while viewing an internal structure of an eyeball.

The OCT imaging apparatus can be used to irradiate an ocular fundus with signal light to obtain information indicating an internal structure in the depth direction at the irradiated position. In this case, the OCT imaging apparatus performs scanning, which is generally known as "B-scan", to obtain a two-dimensional tomographic image of a predetermined cross section of the target to be captured by irradiating a plurality of linearly arrayed positions of the ocular fundus with the above-described signal light.

Further, the OCT imaging apparatus can perform scanning by irradiating a plurality of positions with light in a two-dimensional area of an ocular fundus surface. Thus, the OCT imaging apparatus can finally obtain three-dimensional volume data of the retina.

In a diagnostic observation, comparing two-dimensional tomographic images captured at a plurality of cross sections of a retina is effective to obtain a sufficient amount of information usable in the diagnosis. A conventional technique discussed in Patent Literature 1 allows an operator to designate a target cross section on a fundus image to switch (select) a tomographic image to be displayed on a screen. Further, a conventional technique discussed in Patent Literature 2 can simultaneously display a plurality of tomographic images of a target that are mutually different in the direction of B-scan.

However, when two or more tomographic images are simultaneously displayed, it will be unclear for a viewer if the displayed tomographic images are similar to or different from each other in the direction of B-scan relative to the target to be captured unless information indicating differences is specifically mentioned.

CITATION LIST

Patent Literature

PTL 1: Japanese patent Application Laid-Open No. 2007-117714
PTL 2: Japanese patent Application Laid-Open No. 2008-209166

SUMMARY OF INVENTION

According to an aspect of the present invention, an image processing apparatus is capable of acquiring OCT tomographic images that can be captured by an OCT imaging apparatus configured to scan a target to be captured with low-coherence light along a predetermined main scanning line. The image processing apparatus includes image acquisition means configured to acquire a plurality of OCT tomographic images of the target to be captured along a plurality of main scanning lines that are different in direction, and display control means configured to display the plurality of OCT tomographic images on a display screen using a layout that can express differences in the direction of each main scanning line so as to reflect a relative relationship between respective main scanning line directions with respect to the target to be captured in respective OCT tomographic images.

According to exemplary embodiments of the present invention, the image processing apparatus can determine a layout of respective tomographic images so as to explicitly reflect B-scan direction information on the display screen. Thus, users can easily recognize B-scan directions on the displayed plurality of tomographic images.

Further features and aspects of the present invention will become apparent from the following detailed description of exemplary embodiments with reference to the attached drawings.

BRIEF DESCRIPTION OF DRAWINGS

The accompanying drawings, which are incorporated in and constitute a part of the specification, illustrate exemplary embodiments, features, and aspects of the invention and, together with the description, serve to explain the principles of the invention.

DESCRIPTION OF EMBODIMENTS

Various exemplary embodiments, features, and aspects of the invention will be described in detail below with reference to the drawings.

A tomographic imaging system 100 according to a first exemplary embodiment of the present invention includes an image processing apparatus 110, a tomographic imaging apparatus 120, and a display apparatus 130.

The image processing apparatus 110 determines a display pattern for a plurality of tomographic images captured by the tomographic imaging apparatus 120 in such a way as to indicate a relative relationship between them in a B-scan direction. The image processing apparatus 110 causes the display apparatus 130 to display the plurality of tomographic images according to the determined display pattern.

Figure 1:
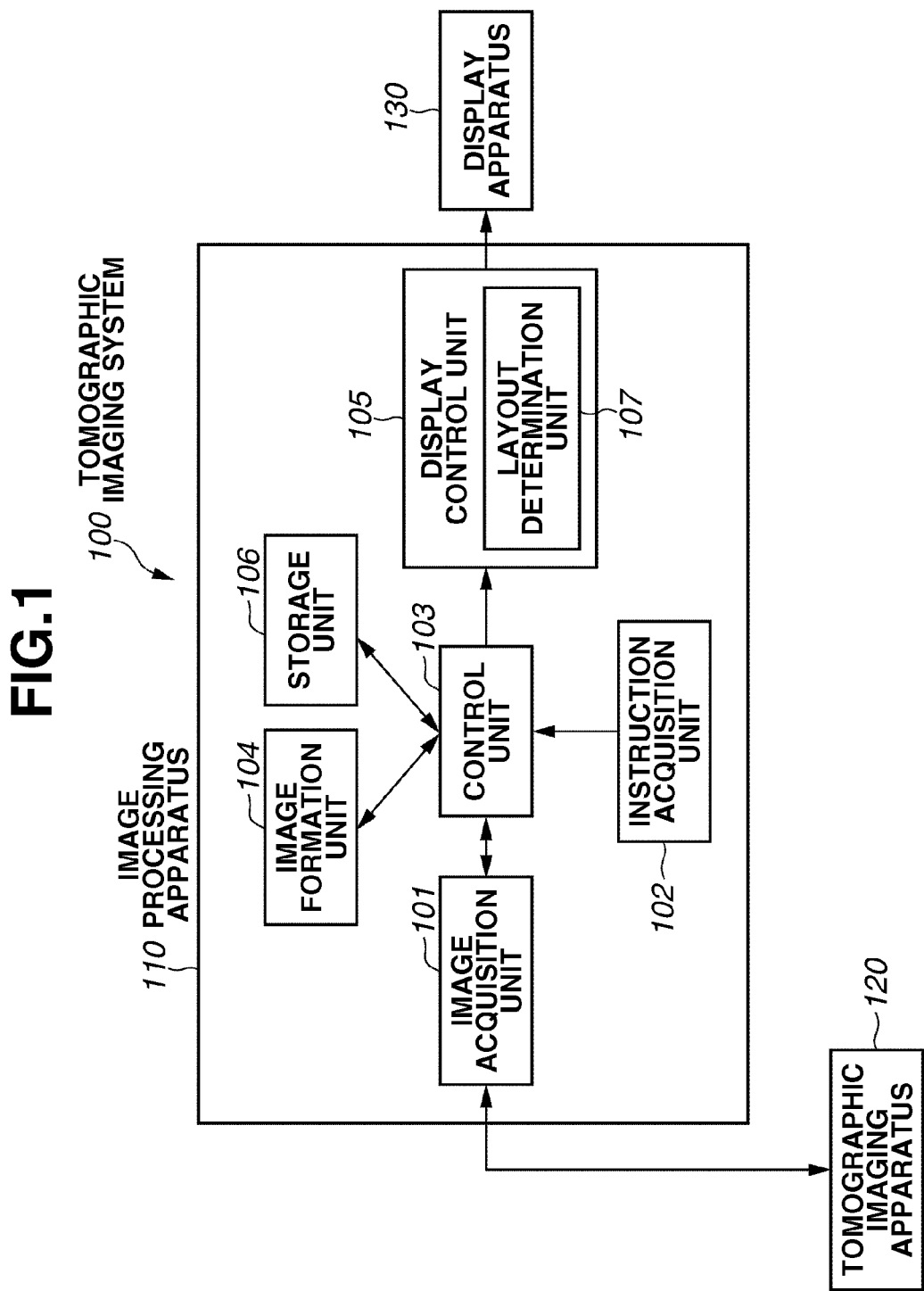
FIG. 1 illustrates an example configuration of a tomographic imaging system according to an exemplary embodiment of the present invention.

FIG. 1 illustrates an example configuration of the tomographic imaging system 100. The tomographic imaging system 100 illustrated in FIG. 1 is an optical coherence tomographic imaging system including the image processing apparatus 110, the tomographic imaging apparatus (e.g., an OCT imaging apparatus) 120, and the display apparatus 130.

The image processing apparatus 110 acquires tomographic images and a fundus image from the OCT imaging apparatus 120 and performs display control for the acquired tomographic images.

Further, the image processing apparatus 110 is functionally operable as a shooting control apparatus that transmits a shooting instruction and shooting conditions to the tomographic imaging apparatus 120. The tomographic imaging apparatus 120 scans a retina of an eye to be diagnosed with signal light to capture tomographic images and a fundus image of the retina, as described below in more detail.

The display apparatus 130 is, for example, a liquid crystal display that can display tomographic images and a fundus image of a target to be captured, tomographic images and a fundus image processed by the image processing apparatus 110, and image capturing control parameters.

The image processing apparatus 110 includes an image acquisition unit 101, an instruction acquisition unit 102, a control unit 103, an image formation unit 104, a display control unit 105, and a storage unit 106.

The image acquisition unit 101 is an input/output unit capable of receiving and transmitting data from and to an external apparatus. The image acquisition unit 101 can acquire tomographic images of a target to be captured from the tomographic imaging apparatus 120. Further, the image acquisition unit 101 acquires an image of a surface of the target to be captured.

In the present exemplary embodiment, the target to be captured is the retina of an eye. Therefore, the image acquisition unit 101 acquires a fundus image, as the image of the surface of the target, which can be captured by a fundus camera. In the present exemplary embodiment, the above-described tomographic images and the fundus image are acquired as two-dimensional images.

Further, the image acquisition unit 101 can transmit and receive data other than images to and from the tomographic imaging apparatus 120. Further, the image acquisition unit 101 can transmit various pieces of information, such as shooting parameters and an image capturing start instruction, which are described below, to the tomographic imaging apparatus 120.

The tomographic imaging apparatus 120 performs a shooting operation based on the received shooting parameters in response to the image capturing start instruction. The image acquisition unit 101 acquires tomographic images from the tomographic imaging apparatus 120, when the tomographic images are captured by the tomographic imaging apparatus 120. In the following description, it is assumed that the tomographic images of the target have been captured along a plurality of main scanning lines that are mutually different in direction.

The instruction acquisition unit 102 can acquire a shooting start instruction and shooting conditions, which are generally input by an operator via an operation unit (not illustrated). The shooting conditions acquired by the instruction acquisition unit 102 include information relating to tomographic image shooting position (i.e., B-scan position), scanning direction, and coherence gate position.

The coherence gate is a value indicating a shooting range of the signal light in the axial direction. The operation unit is, for example, a keyboard and a mouse that are generally provided for the image processing apparatus 110. The instruction acquisition unit 102 transmits an acquired instruction to the control unit 103.

The control unit 103 sets parameters to be required to capture tomographic images, such as signal light shooting position (i.e., B-scan position) and scanning speed, based on the instruction acquired by the instruction acquisition unit 102. Then, the control unit 103 transmits the setting parameters together with a tomographic image capturing instruction and a fundus image shooting instruction to the image acquisition unit 101.

The image acquisition unit 101 performs a shooting operation to capture an image in response to the image capturing instruction. The control unit 103 receives captured images from the image acquisition unit 101 and transmits the acquired images to the image formation unit 104. Further, the control unit 103 transmits images generated by the image formation unit 104 together with the shooting parameters to the display control unit 105.

The image formation unit 104 performs image processing on the obtained tomographic images and the fundus image to obtain sophisticated images that are easy to view and usable in diagnosis. The image processing to be performed by the image formation unit 104 includes, for example, noise reduction processing and contrast adjustment processing applied to an individual image to obtain an image easy to view. For example, the image formation unit 104 can perform the contrast adjustment processing as the above-described formation processing.

First, the image formation unit 104 calculates a histogram distribution for the entire image. Next, the image formation unit 104 sets an upper limit value and a lower limit value. The upper limit value is equal to a maximum value, except for the highest-ranked 5%, in the calculated histogram distribution. The lower limit value is equal to a minimum value, except for the lowest-ranked 5%, in the calculated histogram distribution.

Then, the image formation unit 104 converts each pixel value linearly into one of 256 gradation levels (i.e., from 0 to 255) with reference to the determined upper and lower limit values. In the present exemplary embodiment, the image formation unit 104 can perform gamma correction processing or pseudo-color processing in addition to the above-described contrast adjustment processing. The control unit 103 can transfer the processed images to the display control unit 105.

The display control unit 105 includes a layout determination unit 107. The layout determination unit 107 displays a plurality of OCT tomographic images on a display screen using a layout that can express differences in the direction of each main scanning line so as to reflect a relative relationship between respective main scanning line directions with respect to a target to be captured in respective OCT tomographic images.

In determining the layout of a plurality of tomographic images, the layout determination unit 107 clearly expresses differences in the angle formed between the scanning lines of respective tomographic images based on information indicating a relative positional relationship between the scanning lines (B-scan lines) acquired by the control unit 103.

Further, the display control unit 105 can process (modify) the generated tomographic images and the fundus image based on the parameters in the shooting operation. Further, the display control unit 105 can add new information to the tomographic images and the fundus image. Thus, the display control unit 105 can change a display pattern of the images to be displayed.

The data transmitted by the control unit 103 and received by the layout determination unit 107 includes the B-scan position of each tomographic image relative to the target to be captured, as information obtained from the tomographic imaging apparatus 120. In the present exemplary embodiment, the B-scan position represents the scanning direction of the signal light used by the tomographic imaging apparatus 120. The B-scan is described below in more detail.

The B-scan position can be acquired as additional information independent of the tomographic image, or can be acquired as B-scan positional information associated with each image. Further, the B-scan position can be acquired as instruction information input via the instruction acquisition unit 102, or can be acquired as analyzed information representing the B-scan position obtainable from each image.

If the B-scan position is acquired as additional information independent of the tomographic image, the image acquisition unit 101 can acquire the additional information from the tomographic imaging apparatus 120.

Further, the display control unit 105 can directly acquire information indicating a relative relationship between a plurality of tomographic images in the B-scan direction from the control unit 103. In the present exemplary embodiment, the information indicating the relative relationship is information indicating an angle formed between two or more B-scan directions or a position where two or more tomographic images intersect each other.

The layout determination unit 107 of the display control unit 105 can determine, based on the above-described information, a layout of a plurality of tomographic images in such a way as to indicate the difference in the B-scan position between the tomographic images.

For example, if two images are perpendicular to each other in the B-scan position, the layout determination unit 107 determines a layout of these images in such a way as to incline the orientation of one image by 90 degrees relative to the orientation of the other image. The display control unit 105 performs display control to cause the display apparatus 130 to display the tomographic images according to the determined layout.

The above-described display method is effective to enable a user to intuitively recognize the difference in the B-scan direction between two or more tomographic images. According to the above-described method, users are not required to confirm the B-scan direction each time. User usability can be improved. Display examples are described below in more detail.

The storage unit 106 stores captured tomographic images to be used in diagnosis.

Next, an example configuration of the tomographic imaging apparatus 120 is described below with reference to FIG. 2. The tomographic imaging apparatus 120 is an optical coherence tomographic imaging apparatus that is operable based on the principle of optical coherence tomography (OCT). The tomographic imaging apparatus 120 can obtain a tomographic image by scanning a target to be captured with low-coherence light along a predetermined main scanning line.

The tomographic imaging apparatus 120 acquires a tomographic image of a retina RT of an eyeball EB, which is an example of the target to be captured, by performing scanning with signal light. In the present exemplary embodiment, the tomographic imaging apparatus 120 is a spectral domain type imaging apparatus capable of generating a tomographic image by performing Fourier transform processing on a signal detected by separating interfering light.

In the following description, the Z-axis represents an optical axis direction of the signal light that reaches the target to be captured. The X axis and the Y axis cooperatively define a flat plane that is perpendicular to the Z axis.

Figure 2:
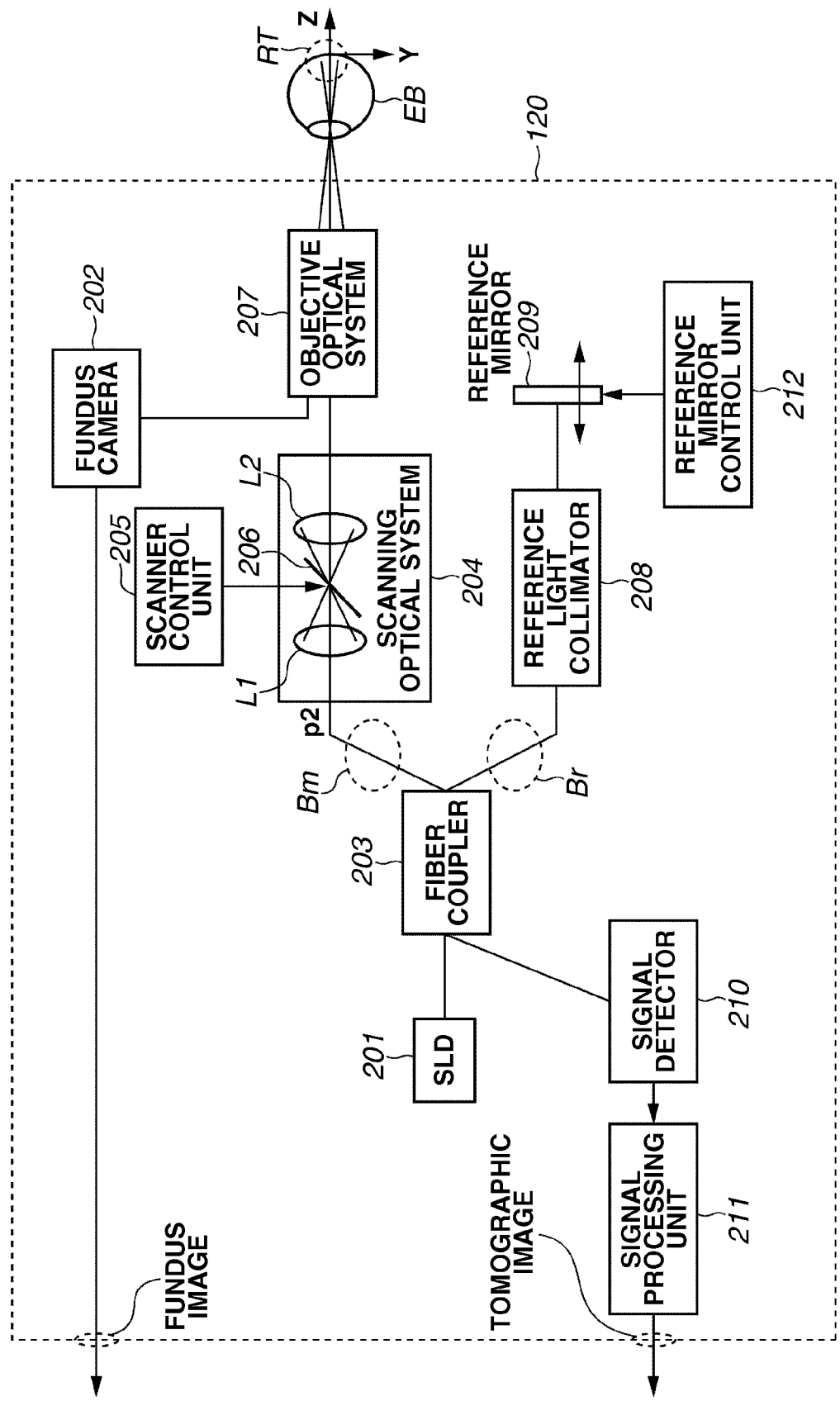
FIG. 2 illustrates an example configuration of a tomographic imaging apparatus according to an exemplary embodiment of the present invention.

In FIG. 2, a fiber coupler 203 receives light emitted from a superluminescent diode (SLD) 201, which serves as a low-coherence light source. The fiber coupler 203 separates the incident light into signal light Bm and reference light Br. The signal light Bm is output via an optical fiber to the scanning optical system 204. The reference light Br is output via an optical fiber to a reference light collimator 208.

The scanning optical system 204 converges the input signal light Bm to a galvanometer mirror 206 and performs scanning of the retina RT by successively changing the incident position of the converged signal light on the retina RT. In the present exemplary embodiment, the galvanometer mirror 206 includes a horizontal scanner that can perform horizontal scanning and a vertical scanner that can perform vertical scanning.

The scanner control unit 205 drives and controls the galvanometer mirror 206. The scanned signal light Bm reaches the retina RT (i.e., an object to be measured) via an objective optical system 207. Then, the signal light reflected from the retina RT sequentially passes through the objective optical system 207 and the scanning optical system 204, and finally reaches the fiber coupler 203.

On the other hand, the reference light Br output from the fiber coupler 203 reaches a reference mirror 209 via the reference light collimator 208. The reference light Br reflected by the reference mirror 209 again reaches the fiber coupler 203. Then, the reference light Br interferes with the signal light Bm in the fiber coupler 203. Thus, the fiber coupler 203 generates interfering light, which can be input to a signal detector 210.

A reference mirror control unit 212 can drive and control the position of the reference mirror 209. The reference mirror control unit 212 can change the optical path length of the reference light Br by changing the position of the reference mirror 209. In other words, the reference mirror control unit 212 can determine the range in which the signal light Bm can interfere with the reference light Br. The above-described range in the Z-axis direction, in which the interfering light can be generated and imaged, is referred to as a coherence gate or a coherent gate.

The signal detector 210 can detect the interfering light generated from the fiber coupler 203 and can output the detected interfering light as an electric interference signal to a signal processing unit (image formation unit) 211. The signal processing unit 211 can perform signal processing (e.g., Fourier transform) on the received interference signal to generate a signal that corresponds to the reflectance along the Z direction of the retina RT.

The signal processing unit 211 reconstructs the tomographic image of the retina RT based on the generated signal. The above-described processing performed to acquire a one-dimensional image is referred to as "A-scan", which represents scanning to be performed in the Z-axis direction. Further, the obtained one-dimensional image is referred to an "A-scan image."

The above-described tomographic imaging apparatus 120 irradiates a predetermined position of the target ocular fundus with the signal light Bm to obtain an A-scan image corresponding to the irradiated position. The tomographic imaging apparatus 120 performs scanning (B-scan) processing along a selected scanning line, at predetermined intervals, by successively changing the above-described predetermined position irradiated with the signal light Bm.

The signal processing unit 211 performs conventionally known interpolation processing to obtain a two-dimensional tomographic image (B-scan image) that extends in the Z-axis direction so as to include the above-described scanning line.

Further, the tomographic imaging apparatus 120 performs A-scan processing in a predetermined area of the target ocular fundus at predetermined intervals. The signal processing unit 211 performs conventionally known interpolation processing on the obtained A-scan image to obtain a three-dimensional tomographic image that includes the above-described predetermined area and extends in the Z-axis direction.

Further, the tomographic imaging apparatus 120 can obtain an arbitrary tomographic image, such as a two-dimensional tomographic image (C scanning image) that visualizes an arbitrary depth region that is substantially parallel to the surface of the target ocular fundus.

In the present exemplary embodiment, the B-scan direction is an arbitrary direction on a flat plane perpendicular to the Z axis. The main scanning line is a line segment connecting irradiation positions of the signal light Bm arrayed along a main scanning direction.

In the present exemplary embodiment, the signal processing unit 211 forms a plurality of tomographic images that are different in the B-scan direction, based on return light of the signal light Bm obtained via the scanning optical system 204 when the retina RT is scanned along a plurality of different B-scan directions.

Further, the tomographic imaging apparatus 120 includes a fundus camera 202 as a unit capable of shooting the ocular fundus of the eyeball EB to be diagnosed where the retina RT (i.e., the target to be captured) is situated. The fundus camera 202 irradiates the ocular fundus with infrared light or visible light as shooting light and forms a fundus image based on reflection light from the ocular fundus.

The objective optical system 207 receives the shooting light emitted from the fundus camera 202 and the signal light emitted from SLD 201. Then, each of the shooting light and the signal light reaches the ocular fundus or the retina RT via the objective optical system 207.

The above-described separation of the optical path by the fiber coupler 203 may be unnecessary if a dichroic mirror having appropriate wavelength selectivity or a comparable optical member is employed. In this case, the optical path can be commonly used. Alternatively, it may also be useful to employ a flip-up mirror.

Figure 3:
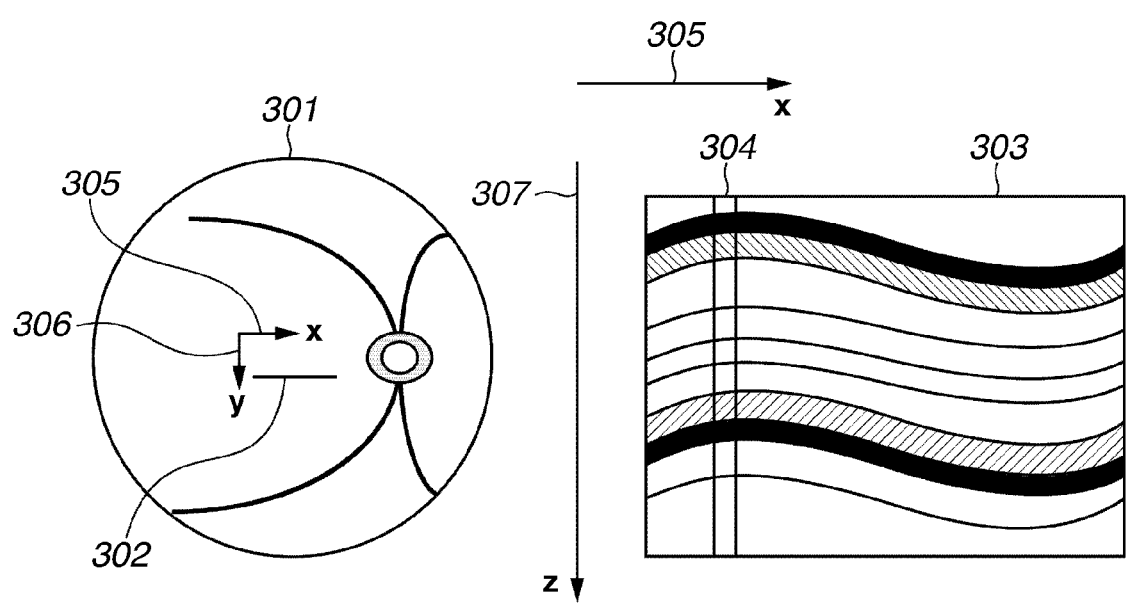
FIG. 3 illustrates an example of a captured image.

An example of the tomographic image that can be captured by the above-described tomographic imaging apparatus 120 is described below with reference to FIG. 3. FIG. 3 illustrates an example of a fundus image 301 of the retina RT of the eye to be diagnosed, which can be captured by the fundus camera 202, and a tomographic image 303 of retinal layers obtained by the tomographic imaging apparatus 120. In general, the retina has a multilayered structure composed of a plurality of retinal layers sequentially positioned in the depth direction as illustrated in FIG. 3.

An X axis 305, a Y axis 306, and a Z axis 307 are employed to define the position in a coordinate system illustrated in FIG. 3. The X axis 305 is parallel to a reference line. The reference line is a straight line passing through the ocular fundus and the macula lutea. The direction of the X axis 305 is identical to a horizontal scanning direction. The Y axis 306 is perpendicular to the X axis 305. The direction of the Y axis 306 is identical to a vertical scanning direction. Both the horizontal scanning direction and the vertical scanning direction are examples of the B-scan direction.

In the following description, although any direction can be set as the B-scan direction, if one of the B-scan directions is selected in a shooting operation, the selected B-scan direction can be referred to as the main scanning direction and a direction perpendicular to the main scanning direction and the A-scan direction can be referred to as a sub scanning direction.

The Z axis 307 is set to be perpendicular to the X axis 305 and the Y axis 306. The Z-axis direction coincides with the optical axis direction of the signal light Bm that reaches the target to be captured. The Z-axis direction also coincides with the A-scan direction. In the present exemplary embodiment, the B-scan direction may be referred to as a scanning direction along which a scanning operation using the signal light Bm is performed (or a direction opposite to the scanning direction), although the B-scan direction is not specifically mentioned referring to positive and negative directions thereof.

To reconstruct the tomographic image 303, the tomographic imaging apparatus 120 moves the galvanometer mirror 206 in the main scanning direction (i.e., in the horizontal direction in the present exemplary embodiment) to cause the signal processing unit 211 to reconstruct the image in each region that corresponds to an A-scan line 304.

Then, the tomographic imaging apparatus 120 performs conventionally known interpolation processing to interpolate a region existing between neighboring A-scan images. Finally, the tomographic imaging apparatus 120 reconstructs the tomographic image 303 as a two-dimensional image or a three-dimensional image.

If the tomographic image 303 obtained in the above-described manner is a two-dimensional image, the obtained tomographic image 303 can be referred to as the B-scan image. In this case, the tomographic image 303 (the B-scan image) corresponds to a two-dimensional cross section that can be defined by the depth direction of the retina and a direction perpendicular to the depth direction.

More specifically, the tomographic image 303 corresponds to a flat plane that can be defined by the X axis 305 and the Z axis 307 illustrated in FIG. 3. Further, a horizontal line 302 illustrated in FIG. 3 represents the B-scan position and the range of the tomographic image 303 when it is seen on the fundus image 301.

An example of processing that can be performed by the tomographic imaging system 100, which can obtain tomographic images at a plurality of different B-scan positions and display the obtained plurality of tomographic images, is described below with reference to a flowchart illustrated in FIG. 4.

In step S410, the instruction acquisition unit 102 acquires shooting conditions input by an operator (not illustrated). The shooting conditions acquired by the instruction acquisition unit 102 include information indicating the shooting position and the scanning direction as well as the coherence gate position (image capturing depth), which are required in the image capturing processing for each of a plurality of tomographic images of the retina of an eye to be diagnosed.

In the present exemplary embodiment, the operator inputs an instruction that designates a portion indicating the retina as the shooting position via the operation unit (not illustrated) of the image processing apparatus 110. The obtained instruction is transmitted to the control unit 103.

In step S420, the image acquisition unit 101 acquires tomographic images and a fundus image from the tomographic imaging apparatus 120. The control unit 103 receives the tomographic images and the fundus image acquired from the tomographic imaging apparatus 120.

The control unit 103 transfers the received images together with information indicating the shooting conditions to the image formation unit 104. In this step, the control unit 103 determines first imaging scan parameters and second imaging scan parameters to be used in a pre-scan operation, which are required to adjust the shooting parameters of tomographic images to be used in the diagnosis.

In the present exemplary embodiment, the scanning direction included in the first imaging scan parameters is set to be parallel to the X direction of the retina as illustrated in FIG. 3. In the following description, the X direction of the retina is referred to as a "first direction." The setting of the shooting range can be performed according to an instruction input via the instruction acquisition unit 102. The shooting range is set to coincide with shooting parameters for a tomographic image to be used in diagnosis.

The control unit 103 determines the shooting position and the shooting direction with respect to the second imaging scanning in such a way as to set a first imaging scanning line to be perpendicular to a second imaging scanning line. The above-described direction is referred to as a "second direction."

The shooting range (scanning distance) is set to coincide with the shooting range of the first image capturing scanning. The control unit 103 transfers the first shooting parameters and the second shooting parameters to the image acquisition unit 101. The first direction is perpendicular to the second direction.

The image acquisition unit 101 transfers the first image capturing parameters and the second image capturing parameters together with image capturing instructions of respective tomographic images to the tomographic imaging apparatus 120.

The tomographic imaging apparatus 120 captures tomographic images of the retina based on the first shooting parameters and the second shooting parameters. The captured tomographic images are referred to as a first tomographic image and a second tomographic image, respectively.

The scanner control unit 205 of the tomographic imaging apparatus 120 drives and controls the galvanometer mirror 206 according to the information indicating the shooting position and the shooting range included in the image capturing parameters transferred from the image acquisition unit 101. The galvanometer mirror 206, which is driven and controlled by the scanner control unit 205, performs scanning using the signal light Bm in both the vertical direction and the horizontal direction on the retina RT.

Further, the tomographic imaging apparatus 120 causes the reference mirror control unit 212 to drive the reference mirror 209 based on coherence gate information included in the image capturing parameters transferred from the image acquisition unit 101.

By driving the reference mirror 209, the tomographic imaging apparatus 120 can change the optical path length of the reference light Br and can obtain a tomographic image in a target depth range of the retina RT. Further, the fundus camera 202 captures a fundus image of the retina RT. The captured fundus image is transferred to the image acquisition unit 101.

Next, an example relationship between image capturing parameters and driving of the galvanometer mirror 206 is described below. The scanning direction designated in the first image capturing parameters is perpendicular to the scanning direction designated in the second image capturing parameters. Therefore, when the scanning direction is set to be horizontal in a case where shooting of a cross section of the retina RT is performed with the first shooting parameters, the galvanometer mirror 206 that corresponds to the horizontal scanning performs a main scanning operation.

On the other hand, when the scanning direction is set to be vertical in a case where shooting of a cross section of the retina RT is performed with the second shooting parameters, the galvanometer mirror 206 that corresponds to the vertical scanning performs a main scanning operation.

In the present exemplary embodiment, image capturing processing based on the first image capturing parameters is first performed. Subsequently, image capturing processing based on the second image capturing parameters is performed. However, the image capturing order can be reversed if it is appropriate.

If the tomographic imaging apparatus 120 includes a plurality of low-coherent light sources, the image capturing processing based on the first image capturing parameters and the image capturing processing based on the second image capturing parameters can be performed simultaneously.

In the present exemplary embodiment, the tomographic image captured based on the first shooting parameters is referred to the first tomographic image. The tomographic image captured based on the second shooting parameters is referred to as the second tomographic image. The image acquisition unit 101 acquires the first tomographic image and the second tomographic image from the tomographic imaging apparatus 120.

In step S430, the image formation unit 104 performs image processing to modify the first tomographic image and the second tomographic image. The image processing to be performed by the image formation unit 104 includes modifying the obtained tomographic image (or fundus image) into an image that is easy to view and usable in diagnosis. Further, the image formation unit 104 can perform gradation conversion processing on a plurality of images in such a way as to have common gradations. In this case, comparison between the images becomes easier.

In step S440, the display control unit 105 performs display control for the first tomographic image and the second tomographic image formed by the image formation unit 104. The layout determination unit 107 checks a relationship between the B-scan direction of the first tomographic image and the B-scan direction of the second tomographic image with reference to the shooting conditions received from the control unit 103.

If it is determined that the above-described two B-scan directions are different from each other, the display control unit 105 determines a layout to change the display pattern of two tomographic images. Then, the display control unit 105 generates data of an image to be displayed based on the determined layout.

In the present exemplary embodiment, the layout determination unit 107 determines the layout of two images so that the relative relationship between two B-scan directions can be stored. One of the two images is fixed and the other is inclined, when they are displayed.

The B-scan direction (shooting direction) of the input first tomographic image is set to be identical to the X-axis direction of the retina illustrated in FIG. 3. Therefore, the layout determination unit 107 determines the layout of the display screen in such a way as to set the depth direction of the retina in the first tomographic image to be parallel to the vertical direction of the display screen of the display apparatus 130.

Further, as the B-scan direction of the second tomographic image is perpendicular to the B-scan direction of the first tomographic image, the layout determination unit 107 determines the layout so as to express the relationship between two B-scan directions. The layout determination unit 107 sets the depth direction of the retina in the second tomographic image to be identical to the horizontal direction of the display screen. Further, the layout determination unit 107 determines a display layout of a fundus image in association with the above-described tomographic images.

The display control unit 105 generates data of an image to be displayed so that the first tomographic image and the second tomographic image can be displayed according to the determined layout. The display control unit 105 transmits the generated data of the image to be displayed to the display apparatus 130. The display apparatus 130 continuously displays the image based on the received data, so as to constitute the display screen, until data of another image to be displayed is newly input. An example of the display screen is described below.

In step S450, the control unit 103 confirms whether the instruction acquisition unit 102 has received a display termination instruction. For example, an operator may instruct the image processing apparatus 110 to capture a new tomographic image via the instruction acquisition unit 102. In this case, the instruction acquisition unit 102 transmits the display termination instruction to the control unit 103.

The operator can instruct the image processing apparatus 110 to start a scanning operation to capture a tomographic image. The instruction acquisition unit 102 has a button (not illustrated) that enables the user to instruct the scanning operation. Alternatively, the operator may press a key of the keyboard or may click on a displayed button on a graphic user interface (GUI) screen.

If the instruction acquisition unit 102 receives a tomographic image shooting start instruction, the instruction acquisition unit 102 transfers the received instruction to the image acquisition unit 101. The image acquisition unit 101 starts a shooting operation to capture a plurality of tomographic images.

In the shooting operation to be performed by the image acquisition unit 101, the main scanning direction of tomographic images is set to be identical to that designated in first tomographic image capturing parameters. The sub scanning direction is set to be identical to that designated in second tomographic image capturing parameters. The image acquisition unit 101 acquires a plurality of tomographic images that are different in the B-scan position.

The tomographic images captured by the image acquisition unit 101 are stored in the storage unit 106. If the instruction acquisition unit 102 receives a new tomographic image shooting start instruction, the processing returns to step S410 in which the instruction acquisition unit 102 newly acquires a shooting instruction.

Further, when a doctor performs diagnosis based on a displayed tomographic image and if a usage termination instruction is later input to the apparatus, the display control unit 105 controls the display apparatus 130 to terminate the display.

Figure 5A:
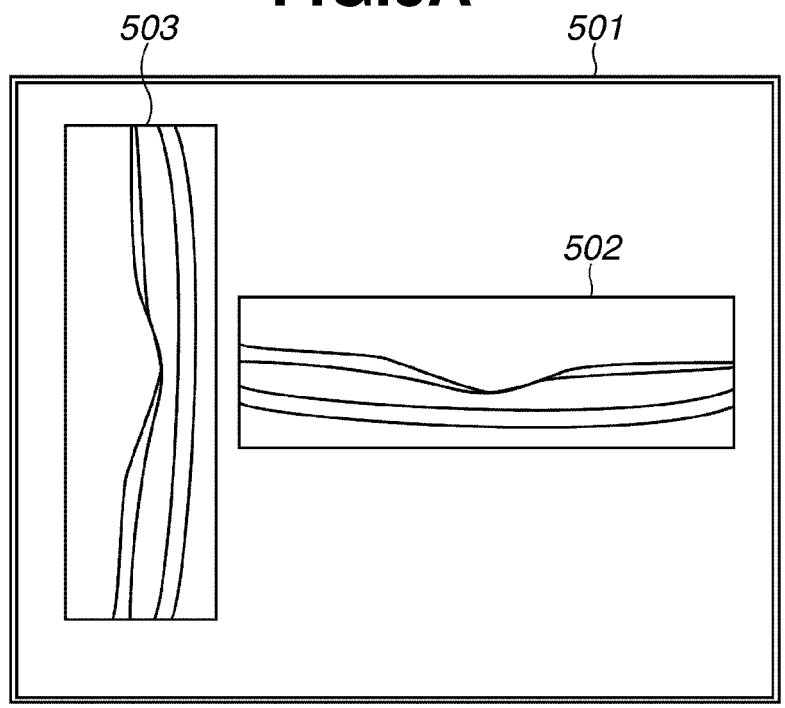
FIG. 5A illustrates a display screen that can be displayed by a display control unit according to an exemplary embodiment of the present invention.

Next, examples of the display screen that can be displayed on the display apparatus 130 by the display control unit 105 are described below with reference to FIGS. 5A and 5B. FIG. 5A illustrates a display screen area 501 of the display apparatus 130. The display screen area 501 includes a first tomographic image 502 and a second tomographic image 503, which are two-dimensionally displayed.

The first tomographic image 502 is an image captured in a state where the X direction of the retina is set to be identical to the B-scan direction. The second tomographic image 503 is an image captured in a state where the Y direction is set to be identical to the B-scan direction.

The display control unit 105 determines the layout of the first tomographic image 502 in such a manner that the vertical direction of the display screen area 501 becomes parallel to the depth direction of the retina (i.e., the Z-axis direction of the retina) in the first tomographic image 502.

Further, the display control unit 105 determines the layout of the second tomographic image 503 in such a manner that the vertical direction of the display screen area 501 becomes perpendicular to the depth direction of the retina (i.e., the Z-axis direction of the retina) in the second tomographic image 503.

In the display screen area 501, the deeper side is positioned on the right side thereof. The B-scan direction of the first tomographic image is perpendicular to the B-scan direction of the second tomographic image.

The display example illustrated in FIG. 5A is an example of two tomographic images whose B-scan lines are not parallel to each other. If the B-scan lines of two tomographic images are parallel to each other, the display control unit 105 determines the layout of two tomographic images to be two-dimensionally displayed in such a manner that the retina depth directions in these tomographic images become parallel to each other.

As described above, the present exemplary embodiment employs the display pattern that can explicitly display a non-parallel relationship between two or more tomographic images if the B-scan lines of these images are not parallel to each other. Therefore, the display apparatus 130 can display the tomographic images together with different B-scan lines thereof on the screen. Users can easily recognize the relative relationship between the tomographic images when these images are displayed on the screen.

The present exemplary embodiment can determine the layout of a plurality of images so as to explicitly indicate the differences in the B-scan line between the displayed images. Therefore, the present exemplary embodiment brings an effect of enabling users to easily and intuitively comprehend the displayed images.

Further, the above-described method for displaying a two-dimensional layout of a plurality of images enables users to accurately obtain information necessary in the diagnosis, compared to a case where a three-dimensional cubic display is employed. If the three-dimensional cubic display is employed, an image displayed on the display screen has a parallelogrammic shape, rather than a rectangular shape. Therefore, if the diagnosis is performed on a three-dimensionally displayed image, the diagnosis may fail.

Figure 5B:
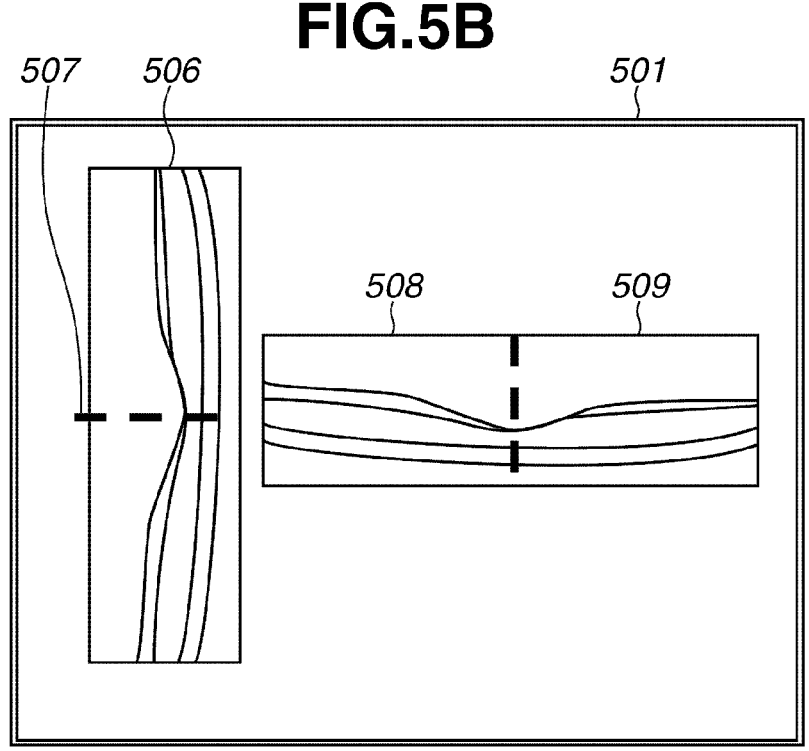
FIG. 5B illustrates another display screen that can be displayed by the display control unit according to an exemplary embodiment of the present invention.

FIG. 5B illustrates another example of the display screen. The display screen illustrated in FIG. 5B includes a display of an intersecting position where two tomographic images intersect, in addition to the illustrated contents of FIG. 5A. The crossing of two tomographic images indicates that cross sections of the target to be captured that correspond to the tomographic images are mutually intersectional.

The display control unit 105 can acquire information indicating the B-scan positions of respective tomographic images from the control unit 103. Therefore, the display control unit 105 can determine whether the tomographic images are intersectional based on the acquired information.

If it is determined that the tomographic images are intersectional, the display control unit 105 adds a mark that indicates the intersecting position where they intersect each other in the scanning of the retina. As an example mark, a line can be used to indicate the intersecting position on the tomographic image. The above-described line, when drawn on the display screen, is parallel to the Z-axis direction of the retina. The first tomographic image and the second tomographic image intersect each other at the position indicated by the added line.

In FIG. 5B, a (dotted line) mark 509 added to the first tomographic image 508 indicates the intersecting position where the first tomographic image 508 intersects with the second tomographic image 506. Further, a (dotted line) mark 507 added to the second tomographic image 506 indicates the intersecting position where the second tomographic image 506 intersects with the first tomographic image 508.

In the present exemplary embodiment, the mark that indicates the intersecting position is not limited to the above-described dotted line. For example, a star mark or any other mark is employable if it is appropriate to indicate the intersecting position. Further, it may be appropriate to add the above-described mark on only one of the first tomographic image and the second tomographic image.

Using the display examples illustrated in FIGS. 5A and 5B enables the display apparatus 130 to indicate that the B-scan lines of respective tomographic images are perpendicular to each other in the depth direction or in the horizontal direction if these tomographic images have been captured along the B-scan lines that are perpendicular to each other.

Even when the above-described display method is employed, targets in respective images may be similar in the structure regardless of differences in the B-scan direction. In such a case, users can comprehend the usage of the inclined layout based on the displayed image even when one of the images is inclined in the display layout as illustrated in FIGS. 5A and 5B.

The retina has a layer structure that is substantially uniform in the entire region. Therefore, the above-described examples can be applied to the layer structure of the retina. In this respect, the above-described examples are display patterns that are effectively employable for tomographic images of the retina.

Further, it is usual in a shooting operation of the retina to set the main scanning direction to be parallel to the reference line passing through the optic disc (optic papilla) and the macula lutea and set the sub scanning direction to be parallel to the Y-axis direction that is perpendicular to the X-axis direction. The diagnosis of tomographic images can be easily performed by disposing an image whose B-scan is performed in the X-axis direction as the first tomographic image 502 without reversing vertical and horizontal sides thereof.

In the above-described exemplary embodiment, the first tomographic image and the second tomographic image are images acquired from the tomographic imaging apparatus 120. However, the present invention is not limited to the above-described examples. It may be useful to acquire images from the data stored in a data server (not illustrated), if these images are usable as the first tomographic image and the second tomographic image.

In this case, in step S420, the image acquisition unit 101 can transmit an acquisition request to the data server (not illustrated) and acquire the first tomographic image and the second tomographic image. The display control unit 105 causes the display apparatus 130 to display the acquired images.

Further, in the above-described exemplary embodiment, the first and second tomographic images are displayed on the display screen. However, the number of images that can be displayed on the display screen is not limited to only two. Three or more images can be displayed.

Further, in step S440 of the above-described exemplary embodiment, the layout determination unit 107 checks the differences in the B-scan position between two or more tomographic images. However, it may be useful to change the display pattern according to the positional relationship between each tomographic image and the target to be captured in the B-scan direction.

Further, it may be useful to put a mark indicating the scanning direction on each displayed tomographic image. The differences in the B-scan direction can be enhanced.

In the above-described exemplary embodiment, the B-scan directions of two images are perpendicular to each other. However, the B-scan directions of two images may intersect at an oblique angle. In such a case, the layout determination unit 107 can employ a layout capable of disposing one of the images obliquely. Alternatively, the layout determination unit 107 can set an angle between two images to be 90 degrees as illustrated in FIGS. 5A and 5B.

In this case, the display control unit 105 displays a character string or a mark that explicitly indicates the intersecting angle between two tomographic images at a position corresponding to the target to be captured. Therefore, the layout of the images can indicate the differences in the B-scan direction as well as the relative positional relationship between the images. Further, instead of displaying a tomographic image obliquely, it may be useful to display a perspective view of the tomographic image.

If the tomographic images are displayed so as to form an angle of approximately 90 degrees, it may be difficult for an operator to confirm the inclined tomographic image. Therefore, it is useful to provide a plurality of display modes. For example, if a first display mode is selected, the display control unit 105 employs the display pattern illustrated in FIGS. 5A and 5B. If a second display mode is selected, the display control unit 105 displays an enlarged image of a selected one of the tomographic images instead of inclining it.

The control unit 103 performs switching of the display mode from the first mode to the second mode in response to operator's selection (or designation) of one of the tomographic images via the operation unit. The display control unit 105 displays an enlarged image of the selected tomographic image without inclining it on the display apparatus 130.

If the operator's selection is cancelled, the control unit 103 changes the display mode from the second mode to the first mode. The display control unit 105 switches the display screen to an ordinary display screen as illustrated in FIG. 3. Performing the above-described operation is effective to enable users to easily view an image while intuitively confirming the B-scan direction.

A second exemplary embodiment of the present invention is characterized in that a fundus image is displayed on the screen in addition to the tomographic images described in the first exemplary embodiment. More specifically, the image processing apparatus selects a display pattern that can superimpose B-scan positions of a plurality of tomographic images on an added fundus image. The display apparatus displays the superimposed B-scan positions in association with the tomographic images.

Further, the second exemplary embodiment is characterized in that the image processing apparatus determines a display layout of the first tomographic image and the second tomographic image considering the shooting direction of each tomographic image to be used in the diagnosis.

More specifically, in the present exemplary embodiment, the display control unit 105 is configured to display a fundus image together with a plurality of tomographic images on a display screen area. Further, the display control unit 105 is configured to superimpose each B-scan position on the fundus image based on information relating to the B-scan position obtained from the control unit 103. Further, the display control unit 105 is configured to display a correspondence relationship between each B-scan position superimposed on the fundus image and a corresponding tomographic image.

Figure 6A:
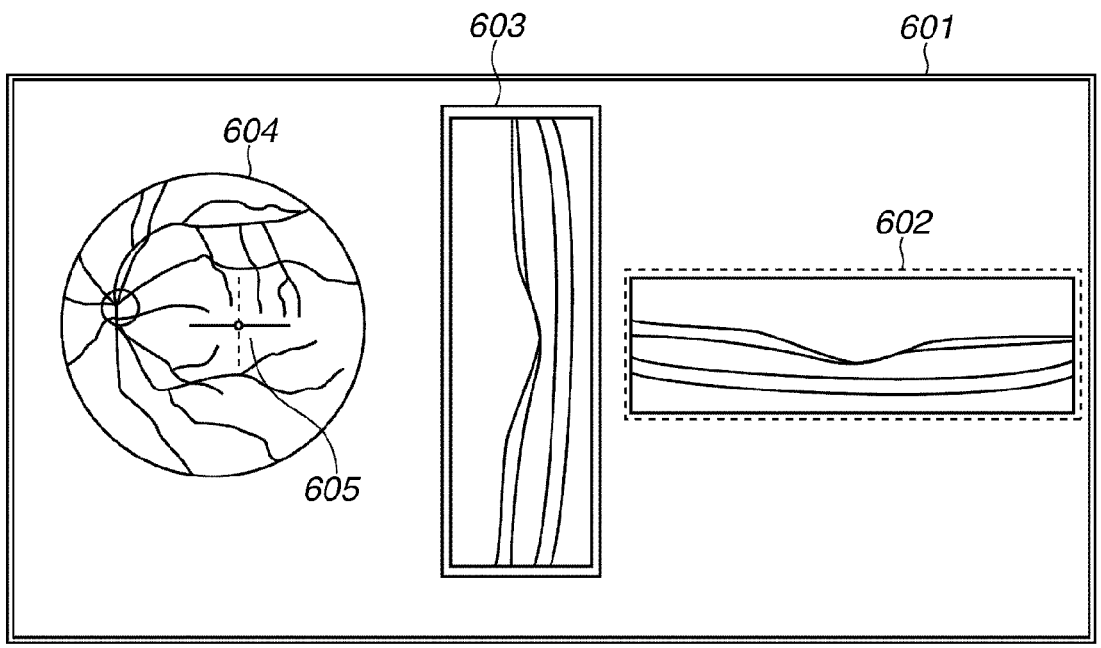
FIG. 6A illustrates a display screen that includes a fundus image together with tomographic images, which can be displayed by the display control unit according to an exemplary embodiment of the present invention.

Examples of the screen that can be displayed on the display apparatus 130 by the display control unit 105 according to the present exemplary embodiment are described below with reference to FIGS. 6A and 6B. FIG. 6A illustrates an example display of a fundus image 604 and an image capturing position 605 where the first tomographic image and the second tomographic image are captured.

In the present exemplary embodiment, the image capturing position 605 is a cross mark that represents both the shooting direction of the first tomographic image and the shooting direction of the second tomographic image.

According to the example illustrated in FIG. 6A, a line segment extending in the Y direction (vertical direction) of the retina in the ocular fundus indicates the B-scan position of the first tomographic image. Further, a line segment extending in the X direction (horizontal direction) of the retina indicates the B-scan position of the second tomographic image, which is perpendicular to the B-scan position of the first tomographic image. The above-described line segments are differentiated in color.

According to the example illustrated in FIG. 6A, the vertically extending line segment is expressed using a dotted line and the horizontally extending line segment is expressed using a solid line, instead of differentiating their colors to discriminate the B-scan position between two tomographic images.

However, the way of discriminating the first tomographic image from the second tomographic image is not limited to the above-described example. For example, it may be useful to determine a frame color of a tomographic image in association with a color of the line segment that indicates a corresponding B-scan position on the fundus image.

Further, the example screen illustrated in FIG. 6A is different from those described in the first exemplary embodiment in that a first tomographic image 602 is a tomographic image that can be obtained by performing scanning in the vertical direction. A second tomographic image 603 is a tomographic image that can be obtained by performing scanning in the horizontal direction.

In short, according to the example screen illustrated in FIG. 6A, it can be known that the main scanning direction in a final shooting operation is set to be identical to the vertical direction of the drawing and perpendicular to the reference line that connects the optic disc and the macula.

In general, the tomographic imaging apparatus 120 performs the main scanning operation in a direction parallel with the reference line. However, the tomographic imaging apparatus 120 may set the main scanning direction in the final shooting to be oblique relative to the reference line if it is desired when the state of a lesion is taken into consideration. FIG. 6A illustrates an example display of a tomographic image having been provisionally captured before the final shooting operation is performed.

As described above, the B-scan direction superimposed on the fundus image is intentionally differentiated from the B-scan direction superimposed on the tomographic image, because the non-inclined display pattern (see the first tomographic image 602) is natural and the confirmation of the image is easy.

In the present exemplary embodiment, easiness in diagnosing a lesion is taken into consideration in the setting of the main scanning direction. Therefore, the display apparatus 130 is required to display an image taken along the main scanning direction in such a way as to enable users to easily view the image to be used in the diagnosis.

In the context of the present disclosure, the provisional shooting is referred to as a shooting to be performed to perform positioning and set shooting conditions required to finally capture a tomographic image. The final shooting is referred to as a shooting to be performed after the above-described provisional shooting is completed.

Figure 6B:
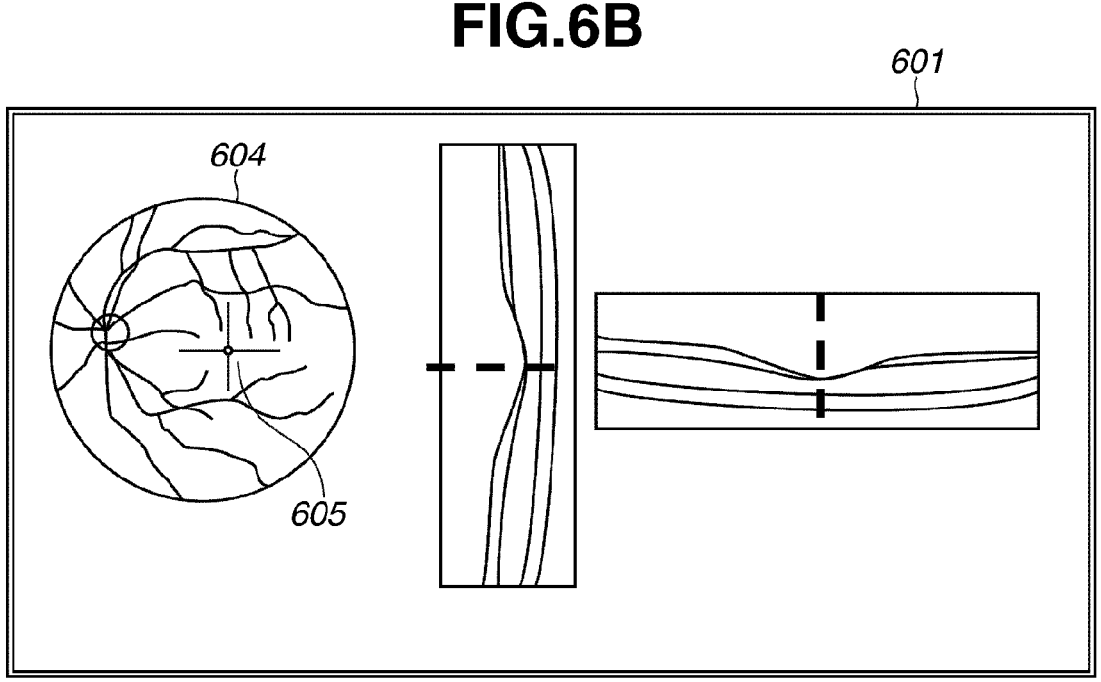
FIG. 6B illustrates another display screen that includes a fundus image together with tomographic images, which can be displayed by the display control unit according to an exemplary embodiment of the present invention.

FIG. 6B illustrates another example of the display screen. Similar to the example screen illustrated in FIG. 5B, two tomographic images are intersectional each other and the crossing position is superimposed on each tomographic image.

On the screen illustrated in FIG. 6B, the layout determination unit 107 determines a layout of two tomographic images in such a manner that the B-scan direction superimposed on the fundus image becomes parallel to the B-scan direction superimposed on the corresponding tomographic image. In this respect, the display pattern illustrated in FIG. 6B is different from the display pattern illustrated in FIG. 6A.

As described above, the display screen illustrated in FIG. 6B is useful in that users can intuitively recognize the relationship between the fundus image and the tomographic images because the B-scan direction of the fundus image coincides with the B-scan direction of the tomographic image.

Employing the display pattern illustrated in FIG. 6A or FIG. 6B enables users to visually compare the fundus image and the tomographic images. Further, superimposing the B-scan position on the fundus image in association with each tomographic image enables users to obtain information effectively usable in the diagnosis by referring to the position of each tomographic image superimposed on the fundus image.

The display patterns according to the present exemplary embodiment are not limited to the above-described examples illustrated in FIGS. 6A and 6B and various display patterns are employable.

As an example, the display control unit 105 can perform switching control in such a way as to display either the fundus image or the tomographic images in response to operator's instruction input via the operation unit.

In this case, if a user inputs an instruction to select the fundus image via the operation unit, the instruction acquisition unit 102 transmits a selection instruction to the control unit 103 in response to the input instruction. The control unit 103 transmits an instruction to the display control unit 105 to select the designated image and perform display switching.

In the present exemplary embodiment, the control unit 103 is functionally operable as a selection unit. In response to the instruction received from the control unit 103, the display control unit 105 selects the first display mode to display the selected fundus image.

Further, in a state where the first display mode is selected, an instruction to select one of the B-scan positions displayed on the fundus image may be input. In this case, the instruction acquisition unit 102 transmits the input instruction to the control unit 103. The control unit 103 transmits an instruction to the display control unit 105 to perform switching of the display. In response to the instruction received from the control unit 103, the display control unit 105 displays the tomographic image that corresponds to the selected B-scan position.

In particular, the above-described switching between two or more display patterns is effective when the fundus image and a plurality of tomographic images are simultaneously displayed in a limited screen area, or when the number of tomographic images to be simultaneously displayed is large.

Instead of using the fundus image that can be captured by the fundus camera 202, it may be useful to display, as an image of the ocular fundus, an integrated image that can be obtained by three-dimensionally integrating tomographic images in the depth direction.

Further, it may be useful that the display control unit 105 displays a simplified image that indicates a relationship between two or more tomographic images at a position corresponding to the target to be captured instead of displaying the fundus image.

An example of the above-described image to be displayed by the display control unit 105 is an image including a circle representing the fundus image and line segments representing B-scan positions located in the circle. The above-described example display is effective if a user wants to confirm the fundus image independent of the tomographic images or when it is required to explicitly display the positional relationship between the tomographic images.

It is desired that the above-described display processing according to the first or second exemplary embodiment is applied to the display of images obtained in a provisional shooting prior to the final shooting.

The display control unit 105 displays the provisionally obtained images on the display apparatus 130 before the final shooting starts. A user performs adjustment of shooting conditions while checking the provisionally obtained images. Even if in the above-described provisional shooting a plurality of tomographic images has been obtained at different B-scan directions, the user can intuitively comprehend the positional relationship between the B-scan directions.

A third exemplary embodiment of the present invention relates to display control for an image captured in a provisional shooting (or pre-scan) operation prior to a final shooting operation.

An example operation that can be performed by the tomographic imaging system 100 is described below. A user instructs adjustment for final shooting conditions while viewing tomographic images and a fundus image displayed on the display apparatus 130 captured as provisional shooting to adjust shooting conditions. The control unit 103 generates new shooting parameters according to an instruction and instructs the tomographic imaging apparatus 120 to perform a shooting operation.

In this respect, the instruction acquisition unit 102 is functionally operable as an adjustment unit configured to adjust shooting conditions for tomographic images of a target to be captured. The display control unit 105 processes the tomographic images so as to correspond to the shooting conditions adjusted according to the input received by the adjustment unit, and causes the display apparatus 130 to display processed images.

As described above, while performing adjustment for the shooting conditions based on user's instruction, the tomographic imaging system 100 transmits a provisional shooting re-shooting instruction via the instruction acquisition unit 102 to the tomographic imaging apparatus 120.

When the adjustment for the shooting conditions has been completed, the user inputs a final shooting instruction. In the present exemplary embodiment, the provisional shooting or the final shooting if performed after the above-described adjustment is referred to as re-shooting.

The tomographic image capturing system according to the present exemplary embodiment is different from the tomographic image capturing system described in the first exemplary embodiment in the processing to be performed in step S450 as described below.

In step S450, the control unit 103 confirms whether the instruction acquisition unit 102 has received a pre-scan shooting termination instruction. The pre-scan shooting termination instruction is, for example, a scanning start instruction to capture a tomographic image to be used in the diagnosis that may be input by an operator via the instruction acquisition unit 102.

Usually, the operator presses a button (not illustrated) of the instruction acquisition unit 102 to input the scanning start instruction to capture a tomographic image to be used in the diagnosis. However, the way of inputting the scanning start instruction is not limited to the above-described example. For example, the operator can press a key of the keyboard or click on a displayed button of the GUI screen.

If the start instruction to capture a tomographic image to be used in the diagnosis is input, the input instruction is transferred to the tomographic imaging apparatus 120 via the image acquisition unit 101. In this respect, the image acquisition unit 101 is functionally operable as an instruction transmission unit. The tomographic imaging apparatus 120 starts capturing a plurality of tomographic images.

The main scanning direction of the tomographic images to be used in the diagnosis is set to be identical to that designated in the first tomographic image capturing parameters. The sub scanning is set to be identical to that designated in the second tomographic image capturing parameters. The tomographic imaging apparatus 120 acquires a plurality of tomographic images at discretely selected positions.

The captured tomographic images to be used in the diagnosis are stored in the storage unit 106. If a tomographic image shooting termination instruction is input, the tomographic imaging apparatus 120 terminates the pre-scan shooting operation.

Figure 4:
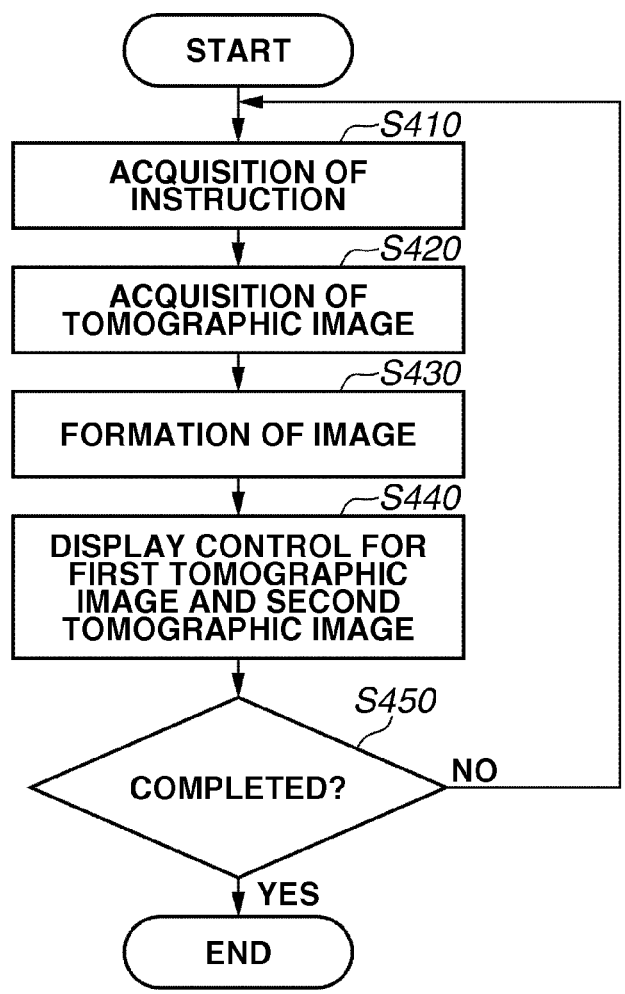
FIG. 4 is a flowchart illustrating an example flow of processing that can be performed by the tomographic imaging system according to an exemplary embodiment of the present invention.

If the tomographic imaging apparatus 120 terminates the pre-scan shooting operation, the tomographic imaging system 100 terminates the processing illustrated in FIG. 4. If the tomographic imaging apparatus 120 continuously performs the pre-scan shooting operation, the processing returns to step S410 in which the instruction acquisition unit 102 newly acquires a shooting instruction.

Figure 7:
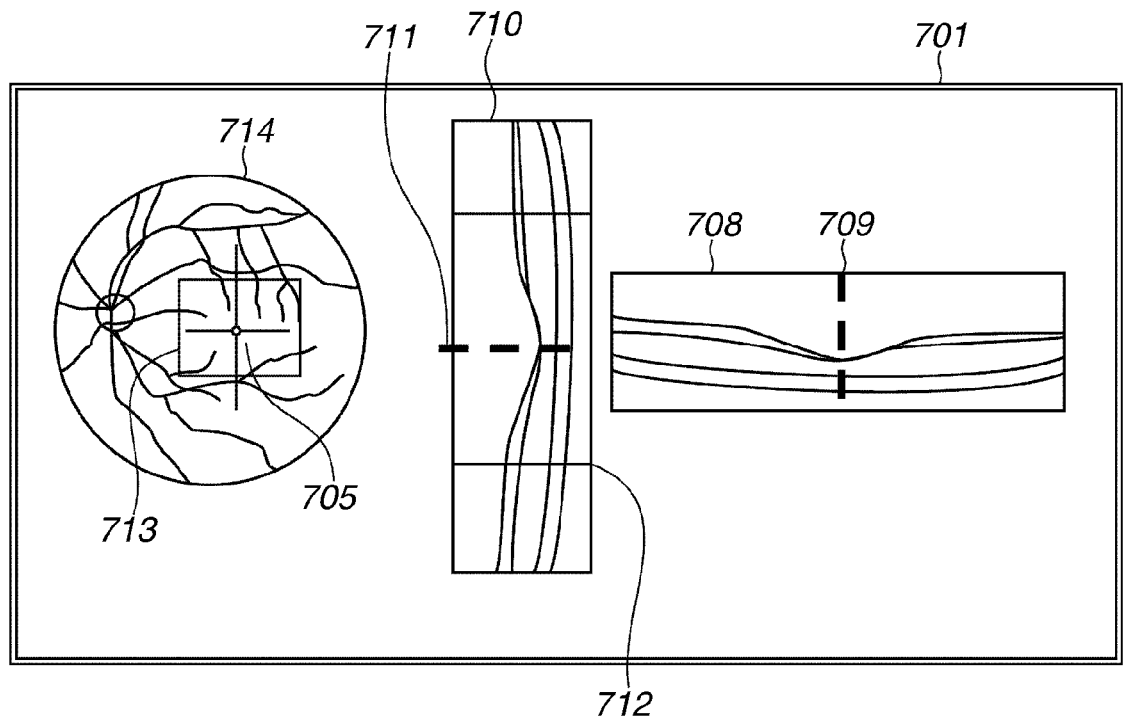
FIG. 7 illustrates another display screen that can be displayed by the display control unit according to an exemplary embodiment of the present invention.

FIG. 7 illustrates a display example of a provisional shooting image when the tomographic imaging apparatus 120 captures tomographic images to be used in the diagnosis from a predetermined area of the retina. The display example illustrated in FIG. 7 includes a first tomographic image 708 and a second tomographic image 710. Further, a mark (dotted line) 709 indicating a crossing position in the second tomographic image 710 is displayed on the first tomographic image 708.

Similarly, a mark (dotted line) 711 indicating a crossing position in the first tomographic image 708 is displayed on the second tomographic image 710. A frame 712 indicating a shooting range of the tomographic image to be used in the diagnosis is also displayed on the second tomographic image 710.

Further, a frame 713 indicating a shooting range of the tomographic image to be used in the diagnosis is displayed on a fundus image 714. The tomographic imaging apparatus 120 performs a shooting operation and the control unit 103 acquires the fundus image 714.

Further, the control unit 103 transfers the captured fundus image, the tomographic images, and shooting conditions (e.g., shooting range) to the display control unit 105. In response to an input, the display control unit 105 performs display control to superimpose the shooting range of the tomographic image to be used in the diagnosis on the fundus image and the tomographic image.

Further, if the instruction acquisition unit 102 acquires a change instruction with respect to the shooting conditions (e.g., shooting range, B-scan position in provisional shooting, and coherence gate) from a user, the control unit 103 generates shooting parameters according to the input instruction and instructs the tomographic imaging apparatus 120 to perform re-shooting via the image acquisition unit 101. The tomographic images re-captured by the tomographic imaging apparatus 120 are input to the image processing apparatus 110 via the image acquisition unit 101, and are displayed on the display apparatus 130 as illustrated in FIG. 7.

When the above-described display method according to the present exemplary embodiment is applied to the display of tomographic images to be captured by the provisional shooting, a user can easily perform setting of a shooting range, selection of a main scanning direction in the B-scan processing, setting of a B-scan position, and adjustment of a coherent gate, while intuitively recognizing a relationship between a plurality of tomographic images. Further, the tomographic imaging system 100 can provide a display screen that enables users to easily recognize the shooting range relative to the fundus image or the tomographic image.

Similar to the display example illustrated in FIG. 6A in the second exemplary embodiment, the display control unit 105 determines the layout in such a way as to display a tomographic image obtained by the B-scan operation performed in parallel to the main scanning direction without inclining it.

For example, if an available apparatus performs provisional shooting while changing the main scanning direction for the B-scan processing and determines the main scanning direction, the adjustment operation can be easily performed.

In general, the tomographic imaging system 100 adjusts the main scanning direction depending on the shape of a lesion. Therefore, the above-described display method according to the present exemplary embodiment brings an effect of enabling users to easily perform image capturing adjustment for an image of a lesion.

A fourth exemplary embodiment of the present invention is characterized in that the tomographic imaging system uses a multi-beam type optical coherence tomographic imaging apparatus, which can simultaneously scan a plurality of positions with a plurality of signal light beams Bm. The tomographic imaging apparatus according to the present exemplary embodiment performs pre-scan image display control before starting a final shooting operation to capture tomographic images to be used in the diagnosis.

The image processing apparatus 110 according to the present exemplary embodiment has a basic configuration similar to that described in the first exemplary embodiment. Therefore, the description relating to the tomographic imaging system 100 is not repeated.

A tomographic imaging apparatus 820 according to the present exemplary embodiment has a configuration different from the above-described tomographic imaging apparatus 120. An example configuration of the tomographic imaging apparatus 820 according to the present exemplary embodiment is described below with reference to with reference to FIG. 8. Components or portions similar to those of the tomographic imaging apparatus 120 are denoted by the same reference numbers and descriptions thereof are not repeated. The tomographic imaging apparatus 820 can use three signal light beams.

Figure 8:
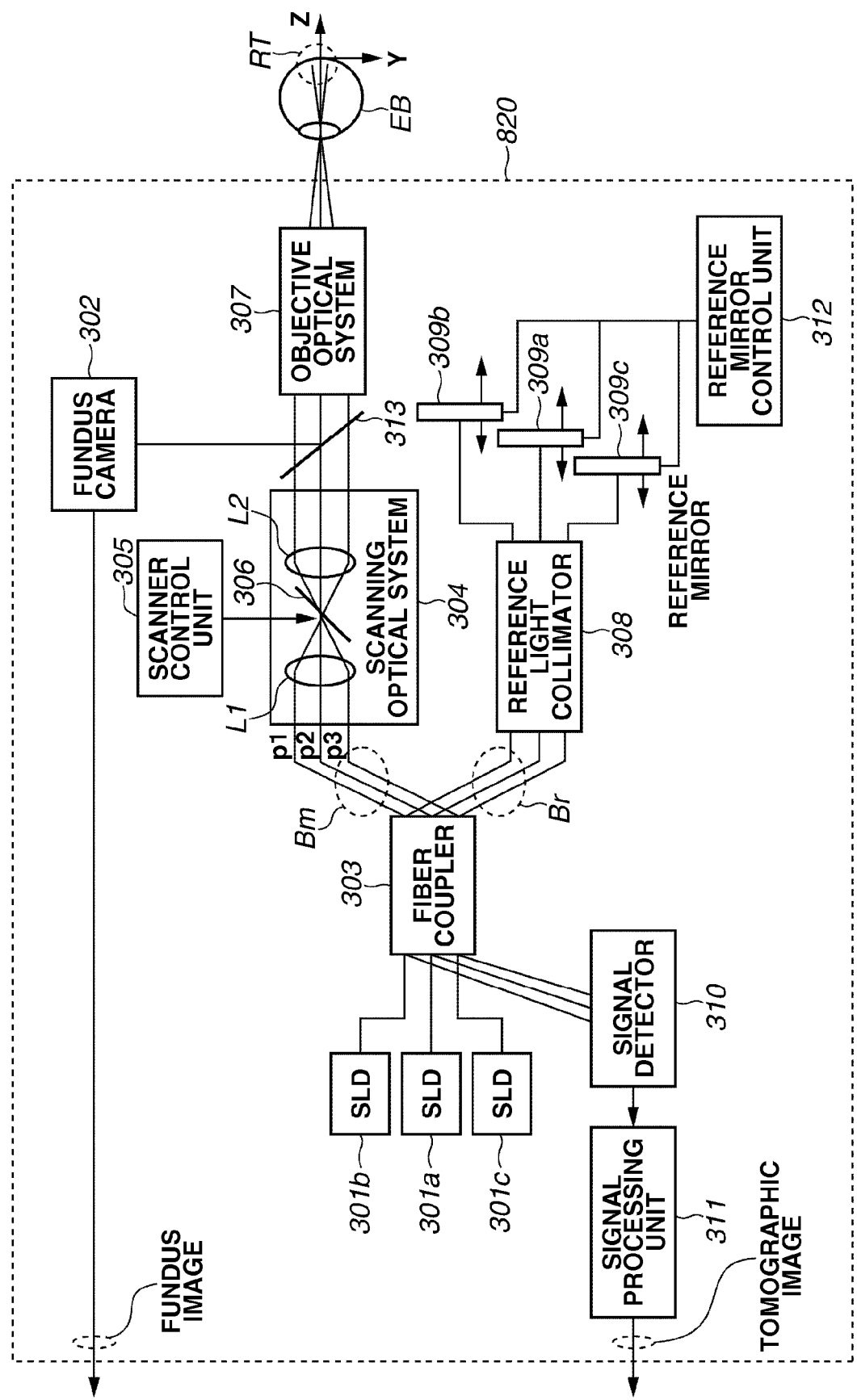
FIG. 8 illustrates an example configuration of a tomographic imaging apparatus according to an exemplary embodiment of the present invention.

In FIG. 8, SLD 301a, SLD 301b, and SLD 301c are low-coherence light sources that can emit light toward a fiber coupler 303. The fiber coupler 303 can separate an incident light flux into a signal light flux Bm and a reference light flux Br. The signal light flux Bm is output via an optical fiber to a scanning optical system 304. The reference light flux Br is output via an optical fiber to a reference light collimator 308.

In the present exemplary embodiment, Bm1 and Br1 represent signal light and reference light that are separated from the light emitted from the SLD 301a. Similarly, Bm2 and Br2 represent signal light and reference light that are separated from the light emitted from the SLD 301b. Further, Bm3 and Br3 represent signal light and reference light that are separated from the light emitted from the SLD 301c.

Three reference light beams Br1, Br2, and Br3 of the reference light flux Br output from the fiber coupler 303 can enter the reference light collimator 308 via optical fibers and can reach a reference mirror 309a, a reference mirror 309b, and a reference mirror 309c, respectively.

The reference light beams Br1, Br2, and Br3 reflected by the reference mirrors 309a, 309b, and 309c again enter the fiber coupler 303. The fiber coupler 303 causes the reference light beams Br1, Br2, and Br3 to interfere with the signal light flux Bm and output interfering light beams that are input to a signal detection unit 310. More specifically, three interfering light beams, which are generated based on the interference between three signal light beams Bm1, Bm2, and Bm3 and the reference light beams Br1, Br2, and Br3, enter the signal detection unit 310.

A reference mirror control unit 312 can drive and control the position of the reference mirror 309a, the reference mirror 309b, and the reference mirror 309c. The signal detection unit 310 can detect each interfering light and output the detected interfering light beams, as three electric interference signals, to a signal processing unit 311.

The signal processing unit 311 can perform signal processing (e.g., Fourier transform) on each interference signal to generate three A-scans that correspond to the reflectance along the Z direction of the retina RT. The signal processing unit 311 can reconstruct three tomographic images of the retina RT based on the generated A-scans.

Figure 9A:
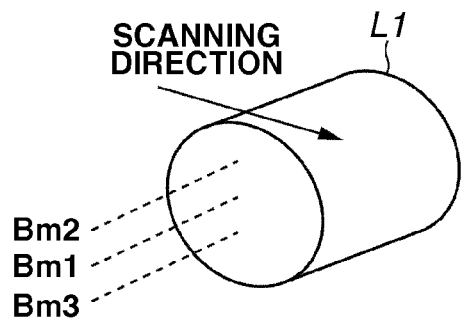
FIG. 9A illustrates an example of signal light beams Bm1, Bm2, and Bm3, which are arrayed along a line perpendicular to a scanning direction.
Figure 9B:
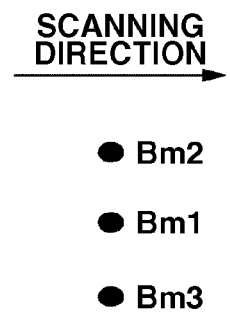
FIG. 9B illustrates the scanning direction of the signal light beams and an alignment of the signal light beams illustrated in FIG. 9A.
Figure 9C:
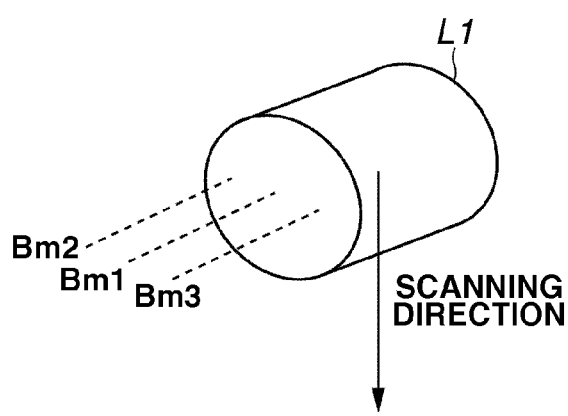
FIG. 9C illustrates an example of signal light beams Bm1, Bm2, and Bm3, which are arrayed along a horizontal direction.

FIGS. 9A to 9E illustrate an example alignment of the signal light beams in the scanning optical system 304. FIG. 9A illustrates an example of the signal light beams Bm1, Bm2, and Bm3, which are arrayed along a line perpendicular to the scanning direction. FIG. 9C illustrates an example of the signal light beams Bm1, Bm2, and Bm3, which are arrayed along a horizontal direction.

Figure 9D:
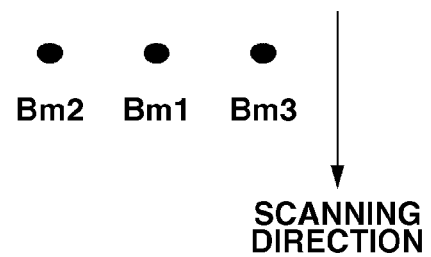
FIG. 9D illustrates the scanning direction of the signal light beams and an alignment of the signal light beams illustrated in FIG. 9C.
Figure 9E:
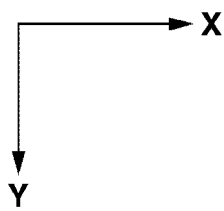
FIG. 9E illustrates an X-axis direction and a Y-axis direction to be applied to FIG. 9A through FIG. 9D.

Further, FIGS. 9B and 9D illustrate the scanning direction of the signal light beams and the alignment of the signal light beams on the retina RT. FIG. 9E illustrates the X-axis direction and the Y-axis direction to be applied to FIG. 9A through FIG. 9D.

Next, an example procedure of processing that can be performed by the image processing apparatus 110 according to the present exemplary embodiment is described below with reference to a flowchart of FIG. 10.

In step S1010, the instruction acquisition unit 102 acquires instruction information input by an operator (not illustrated). The acquired instruction information includes information indicating the shooting position of tomographic images to be used in the diagnosis, the scanning direction in a shooting operation, and the position of a coherence gate (image capturing depth).

For example, the operator designates a predetermined portion of the retina as the shooting position. In the present exemplary embodiment, the tomographic imaging apparatus 820 uses three signal light beams. However, the operator can input only one instruction to designate three shooting positions of the signal light beams. Alternatively, if desired, the measurement position of each signal light beam can be independently instructed.

Further, the instruction acquisition unit 102 acquires an instruction with respect to the layout of three signal light beams. In the present exemplary embodiment, referring to the layout illustrated in FIG. 6A, an example shooting operation that can be performed by scanning the retina in the X direction is described below. The operator can input the shooting instruction via the keyboard (not illustrated) or the mouse (not illustrated) provided for the image processing apparatus 110. The obtained instruction is transmitted to the control unit 103.

In step S1020, the control unit 103 determines first imaging scan parameters and second imaging scan parameters to be used in a pre-scan operation, to adjust the shooting parameters for tomographic images to be used in the diagnosis. In the present exemplary embodiment, the first imaging scan parameters include information indicating the shooting position, the shooting range (scanning distance), the depth, and the direction that are basically identical to those included in the shooting instruction obtained in step S1010.

The second imaging scan parameters include information that determines the shooting position and direction in such a way as to set the second imaging scan to be perpendicular to the first imaging scan at a midpoint of a mutual scanning line.

The shooting range (scanning distance) is set to be identical to that of the first imaging scan. The direction of the first imaging scan is set to be identical to the X direction of the retina. The direction of the second imaging scan is set to be identical to the Y direction of the retina. In the present exemplary embodiment, positive and negative directions of the X-axis direction are not defined.

Further, as three signal light beams are used to perform scanning in the direction of the first imaging scan, the second imaging scan is intersectional with three first imaging scans. In the present exemplary embodiment, the main scanning direction in the final shooting is set to be identical to the horizontal direction.

The above-described determining the first imaging scan parameters and the second imaging scan parameters is a mere example. The parameter determination method is not limited to the above-described example and any other method can be employed if it is appropriate.

In the present exemplary embodiment, only one scanning optical system performs scanning with three signal light beams. Therefore, the system performs the second imaging scan with three signal light beams.

In step S1030, the control unit 103 transfers the first imaging scan parameters and the second imaging scan parameters, which have been determined in step S1020, to the image acquisition unit 101. The image acquisition unit 101 transmits the received parameters to the tomographic imaging apparatus 820.

In step S1040, the tomographic imaging apparatus 820 captures retinal tomographic images and a fundus image based on the first imaging scan parameters and the second imaging scan parameters. In the present exemplary embodiment, the tomographic imaging apparatus 820 performs a first shooting operation by scanning the retina along the X direction, according to the signal light layout illustrated in FIG. 9A.

Therefore, the signal light Bm1, the signal light Bm2, and the signal light Bm3 scan different positions, respectively. Three images to be formed are tomographic images of the target captured at different positions.

Next, the tomographic imaging apparatus 820 scans the retina along the Y direction with the second shooting parameters according to the same signal light layout. Therefore, the signal light Bm1, the signal light Bm2, and the signal light Bm3 are used to obtain tomographic images of the retina at substantially the same positions. As described above, the tomographic imaging apparatus 820 can obtain three tomographic images by performing scanning based on the first imaging scan parameters and obtain three tomographic images by performing scanning based on the second imaging scan parameters.

In step S1050, the control unit 103 acquires the above-described three tomographic images obtained by the first shooting operation and the above-described three tomographic images obtained by the second shooting operation via the image acquisition unit 101. The control unit 103 transfers the acquired tomographic images to the image formation unit 104.

In step S1060, the image formation unit 104 generates images having sufficient image quality usable in the diagnosis based on the tomographic images received from the image acquisition unit 101. In this case, an example of the image generation processing that can be performed by the image formation unit 104 is contrast adjustment processing, gamma correction processing, or pseudo-color processing. The control unit 103 transfers the tomographic images generated in step S1060 to the display control unit 105.

In step S1070, the display control unit 105 performs display control for the generated tomographic images. In the present exemplary embodiment, the tomographic imaging apparatus 820 performs the first shooting operation along a direction parallel to the main scanning direction in the final shooting.

Therefore, the layout determination unit 107 of the display control unit 105 determines a layout of the generated tomographic images in such a way as to set the depth direction of three tomographic images obtained by the first shooting operation to be parallel to the vertical direction of the display screen area. In addition, the layout determination unit 107 determines the layout in such a way as to align three tomographic images in the vertical direction.

The three tomographic images obtained by the second shooting operation are substantially the same in the shooting position. Therefore, to effectively use the display area, the display control unit 105 displays only the tomographic image obtained using the central signal light (i.e., signal light Bm1).

The second shooting direction is perpendicular to the main scanning direction of images to be used in the diagnosis. Therefore, the display control unit 105 performs display control to express the above-described relationship. The layout determination unit 107 of the display control unit 105 determines a layout of the tomographic images in such a way as to set the depth direction of the retina on the tomographic images to be parallel to the horizontal direction of the display screen area and further in such a way as to position pixels of the deeper side on the right side of the display screen area. A display example of the tomographic images according to the layout determined in the present step is described below.

In step S1080, the control unit 103 confirms whether the instruction acquisition unit 102 has received the pre-scan shooting termination instruction. If the pre-scan shooting termination instruction is input, the image processing apparatus 110 terminates the processing illustrated in FIG. 10.

If a pre-scan shooting continuation instruction is input, the processing returns to step S1010, in which tomographic images are captured based on a newly acquired shooting instruction and displayed on the display apparatus 130.

Figure 11A:
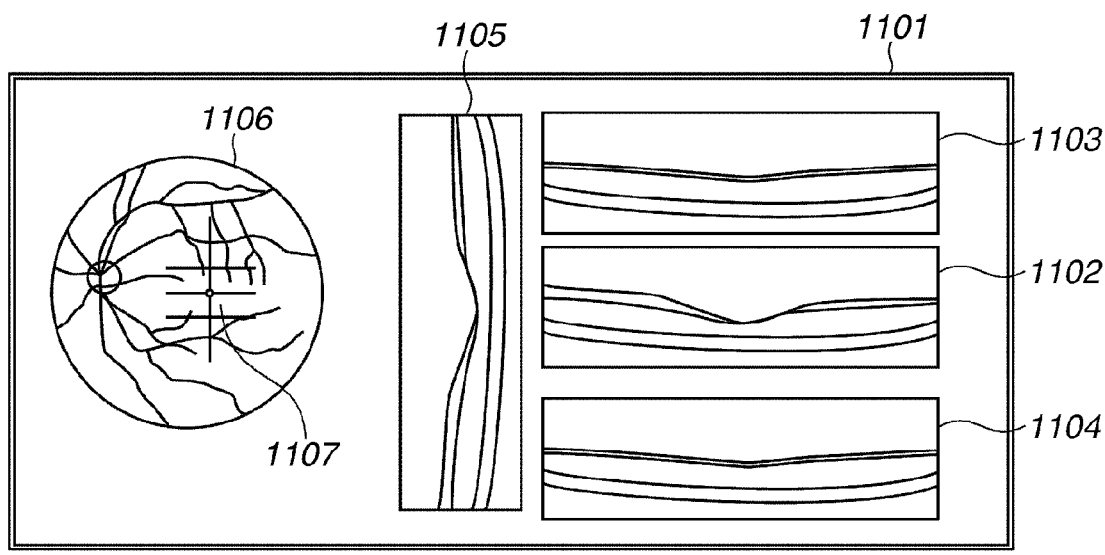
FIG. 11A illustrates an example screen that displays tomographic images captured by a multi-beam type OCT imaging apparatus according to an exemplary embodiment of the present invention.

Examples of the screen that can be displayed on the display apparatus 130 through the above-described processing are described below with reference to FIGS. 11A to 11C. FIG. 11A illustrates a display area 1101 of the display apparatus 130 that includes a tomographic image 1102 obtained using the signal light Bm1, a tomographic image 1103 obtained using the signal light Bm2, and a tomographic image 1104 obtained using the signal light Bm3.

The shooting direction and the shooting range determined to capture the tomographic images 1102, 1103, and 1104 are similar to those included in the shooting parameters to be used in the diagnosis. The depth directions of the tomographic image 1102, the tomographic image 1103, and the tomographic image 1104 (i.e., Z-axis direction of the retina) are set to be parallel to the vertical direction of the display screen area 1101.

Further, the display screen illustrated in FIG. 11A further includes a tomographic image 1105 obtained using the signal light Bm1 so as to correspond to the second shooting direction. The tomographic image 1105 is inclined 90 degrees relative to the horizontal direction of the display screen area 1101. The depth direction of the retina on the tomographic image 1105 is set to be perpendicular to the vertical direction of the display screen. Further, the deeper side is positioned on the right side of the display area.

Further, the display control unit 105 displays a fundus image 1106 on which the B-scan position of each tomographic image is superimposed. The fundus image 1106 can be captured by the tomographic imaging apparatus 820 in step S1040, acquired by the control unit 103 in step S1050, and processed together with tomographic images in step S1060.

Then, in step S1070, the display control unit 105 performs display control to superimpose a B-scan position 1107 of each tomographic image on the fundus image 1106. In FIG. 11A, three lines drawn in the horizontal direction of the display screen represent the B-scan positions of the tomographic image 1102, the tomographic image 1103, and the tomographic image 1104, respectively. A line drawn in the vertical direction represents the B-scan position of the tomographic image 1105.

Figure 11B:
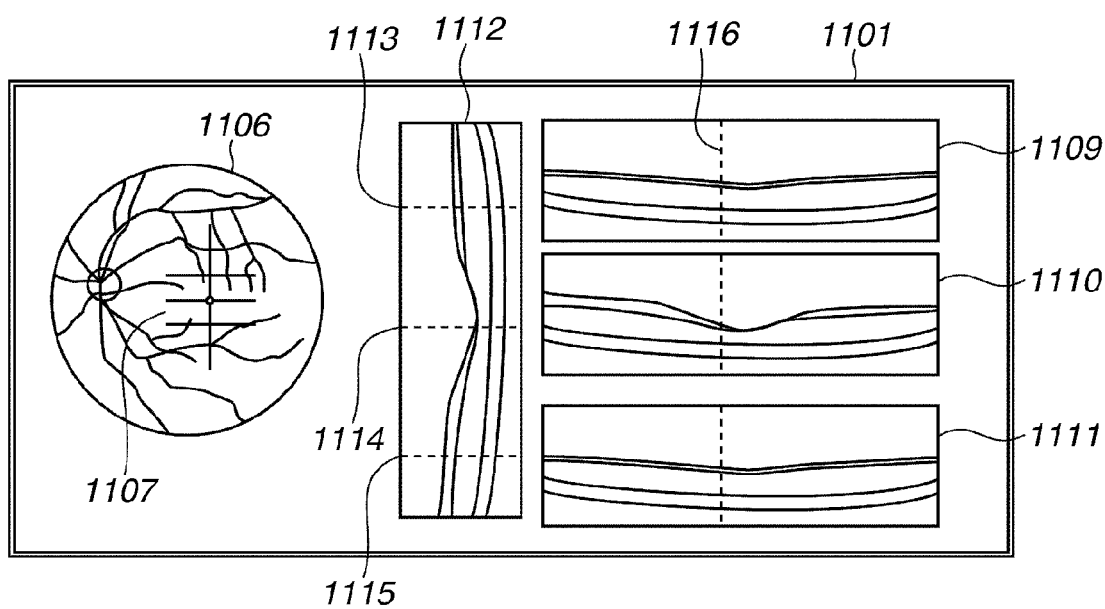
FIG. 11B illustrates another display screen according to an exemplary embodiment of the present invention.

FIG. 11B illustrates another example of the display screen in which an intersecting position of each tomographic image is indicated on the tomographic image. In this case, in step S1060, the display control unit 105 adds a mark indicating the intersecting position of the tomographic image obtained using the signal light Bm1 at the B-scan position extending in the vertical direction on each of the tomographic images obtained using the signal light Bm1, the signal light Bm2, and the signal light Bm3.

Further, the image formation unit 104 adds a mark indicating the intersecting position of each of the tomographic images obtained by the first shooting operation with the signal light Bm1, the signal light Bm2, and the signal light Bm3 on the tomographic image obtained by the second shooting operation with the signal light Bm1.

In FIG. 11B, a dotted line 1116 represents a position where the signal light Bm1 intersects a tomographic image 1110 corresponding to the signal light Bm1. Further, a dotted line 1114, a dotted line 1113, and a dotted line 1115 are added on a tomographic image 1112 obtained by the second shooting operation with the signal light Bm1. The dotted line 1114, the dotted line 1113, and the dotted line 1115 represent the intersecting positions of a tomographic image 1109, the tomographic image 1110, and a tomographic image 1111.

Figure 11C:
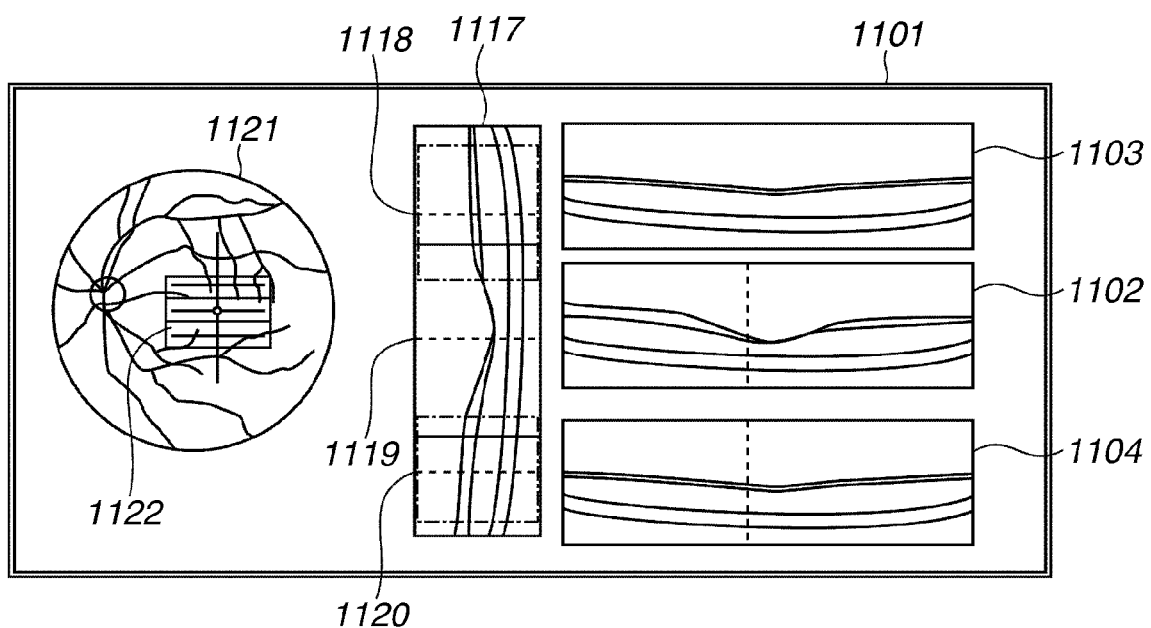
FIG. 11C illustrates another display screen according to an exemplary embodiment of the present invention.

FIG. 11C illustrates another example of the display screen, in which the shooting range of the final shooting operation of each of the signal light Bm1, the signal light Bm2, and the signal light Bm3 is added on the tomographic image 1112 obtained by the second shooting operation with the signal light Bm1. In step S1060, the display control unit 105 adds the above-described information. In FIG. 11C, a frame 1119, a frame 1118, and a frame 1120 are added on a tomographic image 1117 obtained by the second shooting operation with the signal light Bm1. The frame 1119, the frame 1118, and the frame 1120 represent the shooting ranges that correspond to the signal light Bm1, the signal light Bm2, the signal light Bm3, respectively.

As an example, each of the frame 1119 and the frame 1120 is indicated by an alternate long and short dash line. The frame 1118 is indicated by a solid line. The shooting ranges of respective signal light beams are partly overlapped. Further, a frame 1122 is added on a fundus image 1121. The frame 1122 represents a tomographic image measurement area of respective signal light beams.

The above-described configuration enables users to easily recognize a relative relationship between pre-scan tomographic images to be used in the adjustment of shooting parameters that correspond to respective signal light beams when a shooting operation to capture tomographic images to be used in the diagnosis is performed with simultaneously used plurality of signal light beams.

The above-described exemplary embodiment has described a selective display of the tomographic image based on the signal light Bm1 when the tomographic image obtained by the second shooting operation is displayed. However, the present invention is not limited to the above-described selection. For example, it may be useful to display the tomographic image based on the signal light Bm2 or the tomographic image based on the signal light Bm3. Further, it may be desired to display two or more tomographic images.

Further, it may be useful that the tomographic imaging apparatus 820 uses only one signal light to capture tomographic images. In this case, for example, the tomographic imaging apparatus 820 performs measurement using the signal light Bm1 and does not display tomographic images corresponding to the signal light Bm2 and the signal light Bm3 when the pre-scan tomographic images are displayed.

In the present exemplary embodiment, to capture tomographic images to be used in the diagnosis, the tomographic imaging apparatus 820 uses three signal light beams. However, the number of signal light beams is not limited to three and can be two or can be four or more. In these cases, the tomographic imaging apparatus performs a pre-scanning operation with respective signal light beams and the display apparatus 130 displays the captured tomographic images.

Further, the present invention is not limited to the above-described exemplary embodiment and can be applied to an optical coherence tomographic imaging apparatus that can independently control three signal light beams to perform scanning. In such a case, the display method according to the present invention is effective when the complicatedness in adjustment is taken into consideration.

A fifth exemplary embodiment of the present invention provides a tomographic imaging system that can explicitly display a relationship between a plurality of signal light beams in coherence gate position (image capturing depth). To this end, the tomographic imaging system according to the present exemplary embodiment determines a limited number of tomographic images to be displayed among a plurality of tomographic images captured with different signal light beams.

Further, the tomographic imaging system according to the present exemplary embodiment can generate and display a new second tomographic image by combining second tomographic images captured using a plurality of signal light beams.

The image processing apparatus 110 according to the present exemplary embodiment has a basic configuration similar to that described in the first exemplary embodiment (see FIG. 1). Therefore, the description relating to the tomographic imaging system 100 is not repeated. Further, a tomographic imaging apparatus according to the present exemplary embodiment is similar to that tomographic imaging apparatus 820 described in the fourth exemplary embodiment. Therefore, the description relating to the tomographic imaging apparatus is not repeated.

Next, an example procedure of processing that can be performed by the image processing apparatus 110 according to the present exemplary embodiment is described below with reference to the flowchart illustrated in FIG. 10. In the following description, processing different from that described in the fourth exemplary embodiment is described in detail and the descriptions for the rest is not repeated.

In step S1010, the instruction acquisition unit 102 acquires instruction information input by an operator (not illustrated). The acquired instruction information includes information indicating the shooting position of tomographic images to be used in the diagnosis, the B-scan direction in a shooting operation, and the position of a coherence gate (image capturing depth).

In the present exemplary embodiment, it is assumed that the operator can independently designate adjustment of the coherence gate with respective signal light beams. The instruction acquisition unit 102 transmits the obtained instruction to the control unit 103.

In step S1040, the tomographic imaging apparatus 820 captures retinal tomographic images based on first shooting parameters and second shooting parameters. In addition, the fundus camera 302 captures a fundus image. In the present exemplary embodiment, similar to the fourth exemplary embodiment, the tomographic imaging apparatus 820 performs the first shooting operation by scanning the retina along the X direction, according to the signal light layout illustrated in FIG. 9A.

Therefore, the tomographic imaging apparatus 820 captures tomographic images at different cross sections with the signal light Bm1, the signal light Bm2, and the signal light Bm3, respectively. Next, the tomographic imaging apparatus 820 scans the retina along the Y direction with the second shooting parameters according to the same signal light layout.

Therefore, the signal light Bm1, the signal light Bm2, and the signal light Bm3 obtain tomographic images of the retina at substantially the same positions. Thus, the tomographic imaging apparatus 820 can obtain three tomographic images by performing scanning based on the first shooting parameters and obtain three tomographic images by performing scanning based on the second shooting parameters.

In the present exemplary embodiment, the tomographic imaging apparatus 820 adjusts the coherence gate position of each signal light, i.e., the optical path length of the reference light Br. Therefore, the control unit 103 controls the reference mirror control unit 312 to adjust the positions of the reference mirrors 309a, 309b, and 309c that correspond to the signal light beams Bm1, Bm2, and Bm3. The tomographic imaging apparatus 820 captures first tomographic images and second tomographic images for each signal light at the adjusted same coherence gate position (image capturing depth).

In step S1060, the image formation unit 104 forms three first tomographic images and three second tomographic images. In the present exemplary embodiment, the image formation unit 104 generates a composite second tomographic image by combining a plurality of second tomographic images corresponding to different signal light beams in addition to the image formation processing (e.g., contrast adjustment).

The image formation unit 104 can perform at least one of the following processing, as example generation processing.

(a) The image formation unit 104 generates a composite second tomographic image by partly segmenting (clipping) image portions from the second tomographic images corresponding to a plurality of signal light beams. In this case, an area to be segmented or clipped is set to be identical to an area in which a tomographic image to be used in the diagnosis is captured with each signal light.

(b) The image formation unit 104 mixes second tomographic images corresponding to all of the signal light beams. In this case, the image formation unit 104 can generate an average tomographic image that represents the second tomographic images corresponding to all of the signal light beams. Alternatively, the image formation unit 104 can generate an average tomographic image by weighting the second tomographic image of each signal light. For example, a weighting factor 2 can be allocated to a second tomographic image corresponding to signal light 1, while a weighting factor 1 can be allocated to a second tomographic image corresponding to another signal light.

The generation processing according to the present invention is not limited to the above-described example. For example, it is useful to generate a composite second tomographic image based on second tomographic images corresponding to a plurality of signal light beams.

In step S1070, the display control unit 105 performs display control for the three first tomographic images, the three second tomographic images, and the composite second tomographic image, which have been formed in step S1060.

The layout determination unit 107 of the display control unit 105 determines a layout of respective tomographic images in such a way as to set the depth direction of the three first tomographic images to be parallel to the vertical direction of the display area and further in such a way as to position the pixels of the deeper side on the lower side of the display area.

The display control unit 105 displays the three first tomographic images on the display apparatus 130 according to the layout determined by layout determination unit 107. The display control unit 105 performs display control for one of the second tomographic images corresponding to the three signal light beams and the composite second tomographic image obtained in step S1060.

In the present exemplary embodiment, the display control unit 105 performs display control for the composite second tomographic image. The image capturing direction of the second tomographic images corresponding to respective signal light beams is perpendicular to the shooting direction defined in the image capturing parameters to be used in the diagnosis. Therefore, the display control unit 105 displays the above-described relationship.

More specifically, the layout determination unit 107 of the display control unit 105 determines a layout of respective images in such a way as to set the depth direction of the composite second tomographic image to be parallel to the horizontal direction of the display area and further in such a way as to position the pixels of the deeper side on the right side of the display area. The display control unit 105 displays the composite second tomographic image on the display apparatus 130 according to the layout determined by layout determination unit 107.

The second tomographic image to be displayed is not limited to the above-described composite second tomographic image. Further, it may be desirable to switch the second tomographic image to be displayed while the image processing apparatus according to the present invention is operating.

For example, an operator may momentarily adjust image capturing parameters, such as the coherence gate position (image capturing depth), for a specific signal light. In such a case, in step S1070, the display control unit 105 can display a second tomographic image corresponding to the concerned signal light.

Figure 12A:
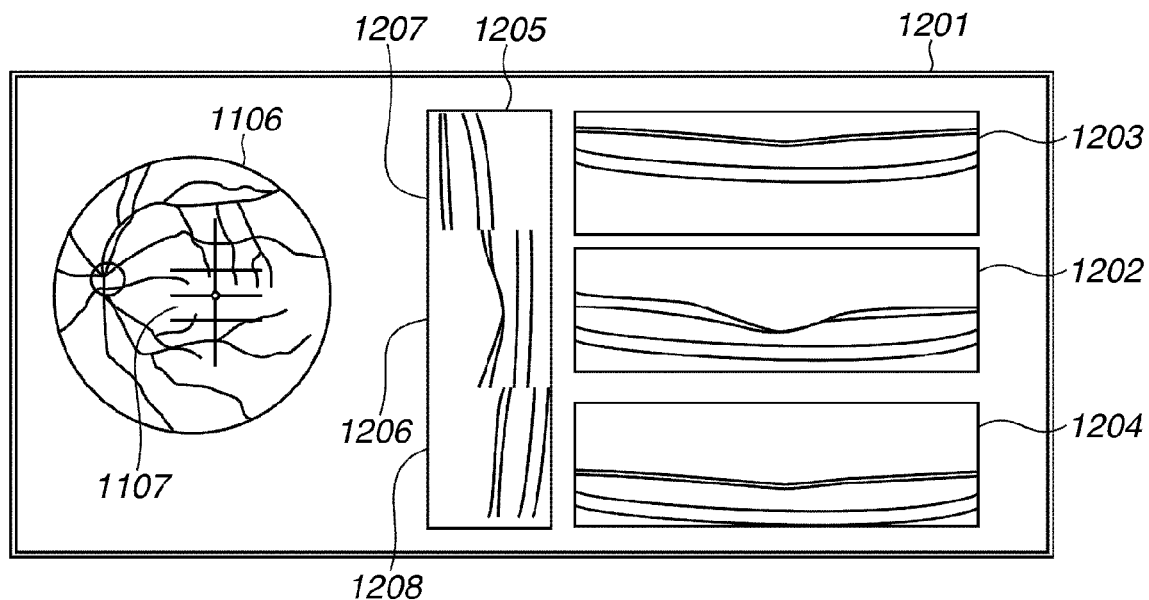
FIG. 12A illustrates an example display screen that displays a relative positional relationship between coherence gates corresponding to respective signal light beams according to an exemplary embodiment of the present invention.
Figure 12B:
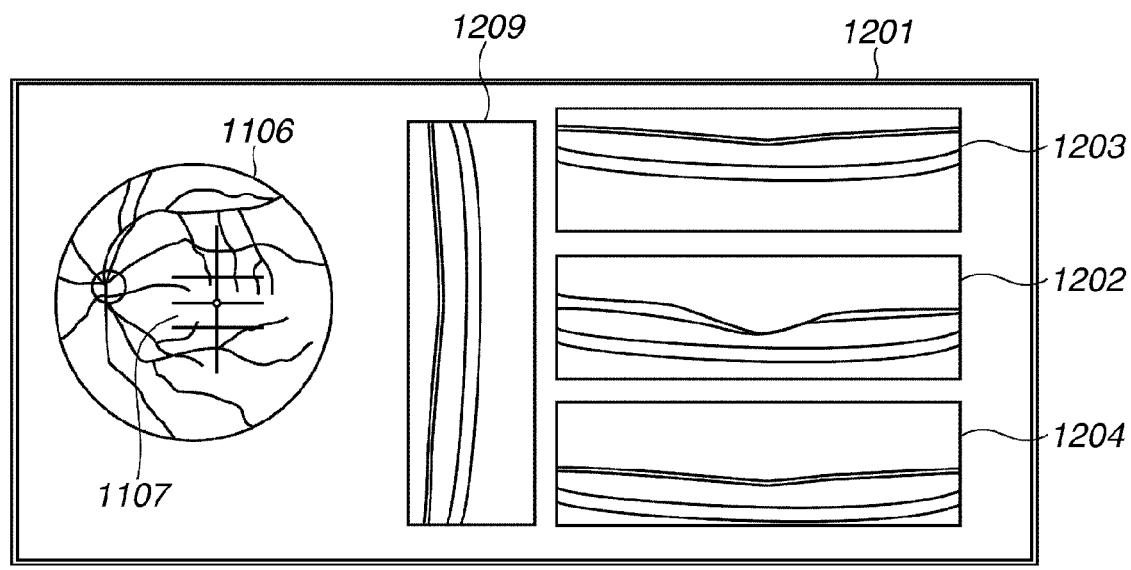
FIG. 12B illustrates an example display screen that is usable to adjust the position of each coherence gate according to an exemplary embodiment of the present invention.

FIGS. 12A and 12B illustrate display examples that can be displayed on the display apparatus 130 by the display control unit 105 according to the present exemplary embodiment. FIG. 12A illustrates a first tomographic image 1202 that corresponds to the signal light Bm1, a first tomographic image 1203 that corresponds to the signal light Bm2, and a first tomographic image 1204 that corresponds to the signal light Bm3, which are disposed in a display area 1201 of the display apparatus 130.

The shooting direction and the shooting range having been set for the tomographic images 1202, 1203, and 1204 are similar to those defined in the tomographic image information parameters to be used in the diagnosis. The depth direction (Z direction of the retina) of the first tomographic image 1202, the first tomographic image 1203, and the first tomographic image 1204 is set to be identical to the vertical direction of the display area 1201.

The depth direction (Z direction of the retina) of a composite second tomographic image 1205 obtainable from the second tomographic images corresponding to the three signal light beams is set to be identical to the horizontal direction of the display area 1201. Further, a deeper side of the second tomographic image 1205 is positioned on the right side of the display area 1201.

The composite second tomographic image 1205 includes an area 1206, an area 1207, and an area 1208, which are extracted from the same area of the second tomographic images corresponding to signal light 1, signal light 2, and signal light 3, respectively.

FIG. 12B illustrates a second tomographic image 1209 corresponding to the signal light 2 displayed in the display area 1201 of the display apparatus 130, in a case where the signal light 2 is a target to be operated to adjust the coherence gate position.

According to the above-described configuration, not only a relative relationship between image capturing positions of respective signal light beams on the retina but also a relative relationship between coherence gates can be easily recognized by performing the display control for the first tomographic images and the second tomographic image that correspond to the signal light beams.

Figure 13A:
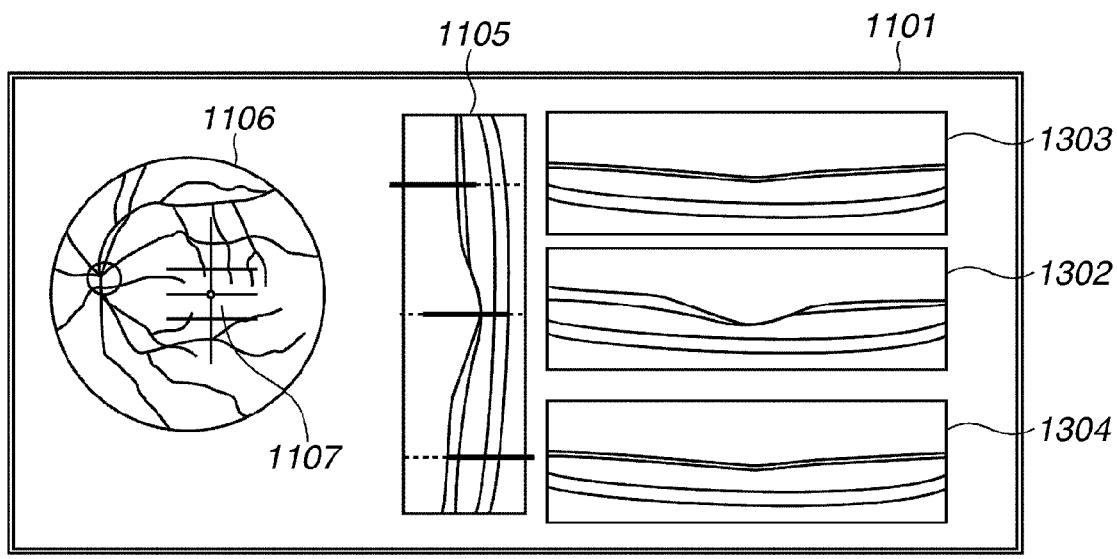
FIG. 13A illustrates an example display screen that displays a relative positional relationship between coherence gates corresponding to respective signal light beams according to an exemplary embodiment of the present invention.
Figure 13B:
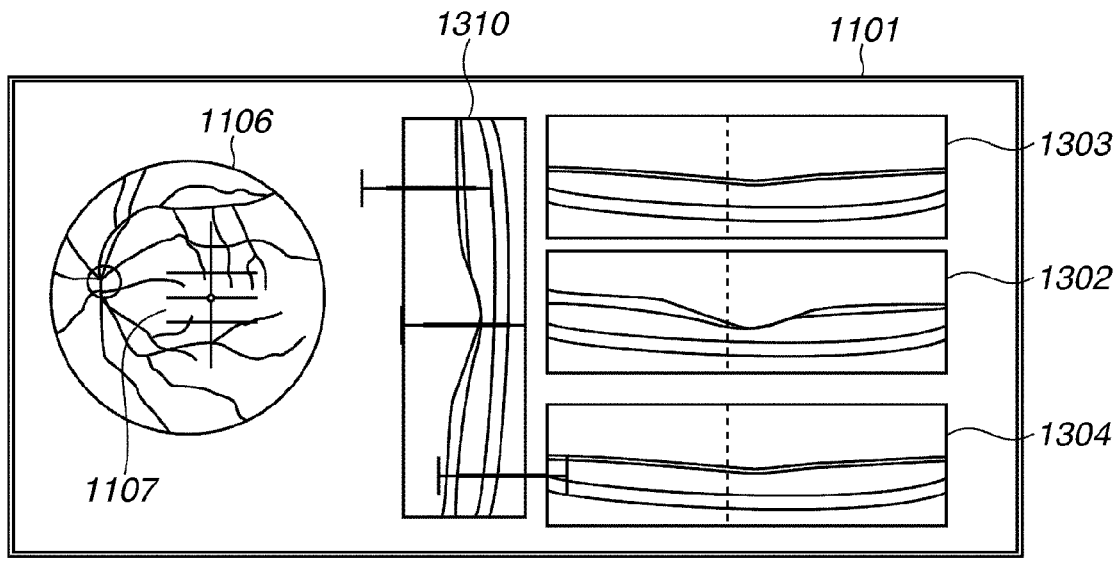
FIG. 13B illustrates another example display screen according to an exemplary embodiment of the present invention.
Figure 13C:
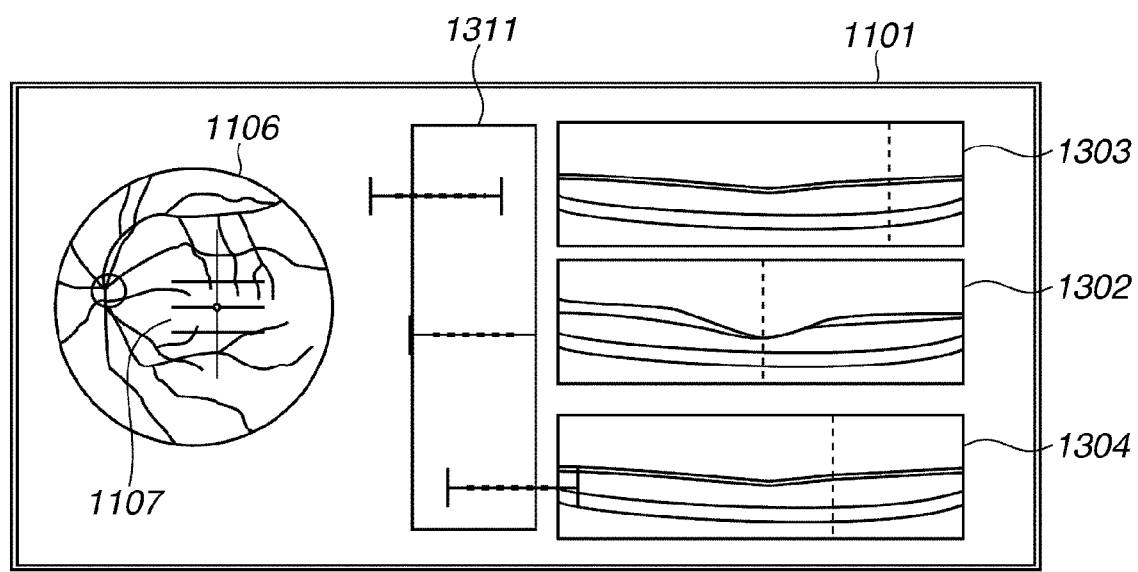
FIG. 13C illustrates another example display screen according to an exemplary embodiment of the present invention.

FIGS. 13A to 13C illustrate display examples that can display coherence gate positions of respective each signal light beams. The display screen illustrated in FIG. 13A is different from the display screen illustrated in FIG. 11B in that a coherence gate relative relationship display is added. Descriptions for portions similar to those already described with reference to FIG. 11B are not repeated.

In FIG. 13A, dotted lines represent positions where first tomographic images 1302, 1303, and 1304 intersect with the second tomographic image 1105. Further, each bold line represents a coherence gate position. The above-described display is easy to see and applicable to different signal light beams with respect to a coherence gate relative positional relationship between tomographic images captured at different scanning positions. Thus, users can easily adjust the coherence gate.

FIG. 13B and FIG. 13C illustrate other display examples that can dynamically change the coherence gate during a B-scan image capturing operation. A second tomographic image 1310 illustrated in FIG. 13B includes solid lines each indicating the position of the coherence gate of a corresponding first tomographic image.

It is usual that the coherence gate may change during a tomographic image capturing operation. In FIG. 13B, a thin solid line indicates a variation width of the coherence gate. A bold solid line indicates a portion constantly included in the coherence gate range. Thus, the display method illustrated in FIG. 13B can effectively display the variation width of the coherence gate and the stationary shooting range in a case where the coherence gate is variable during a tomographic image capturing operation. Users can compare the different tomographic images with respect to the coherence gate.

Further, in FIG. 13C, each thin solid line indicates the variation width of the coherence gate. Further, the display area 1101 includes dotted lines indicating A-scan positions of the first tomographic images 1302, 1303, and 1304. Further, a dotted line representing the coherence gate position corresponding to the dotted line indicating the A-scan is superimposed on the display of the coherence gate variation width. In response to a change of the designated A-scan position, the display of the coherence gate is variable within the width range indicated by the thin solid line. Further, the display example illustrated in FIG. 13C does not include the above-described second tomographic image.

The display control unit 105 performs the above-described display control. The above-described display enables users to easily confirm the coherence gate corresponding to each position of the tomographic image. Further, the above-described display enables users to confirm the coherence gate positional relationship between different tomographic images.

The display control method described in the above-described exemplary embodiment can explicitly indicate the relative relationship between respective signal light beams during image capturing processing. The tomographic imaging system according to a sixth exemplary embodiment of the present invention can perform display control for enabling users to easily recognize the signal light that is currently adjusted.

A basic configuration of the image processing apparatus 110 according to the present exemplary embodiment is similar to that described in the first exemplary embodiment with reference to FIG. 1. Therefore, the description of the image processing apparatus 110 is not repeated. Further, a tomographic imaging apparatus according to the present exemplary embodiment is similar to that described in the fourth exemplary embodiment (see FIG. 8). Therefore, the description of the tomographic imaging apparatus is not repeated.

Figure 10:
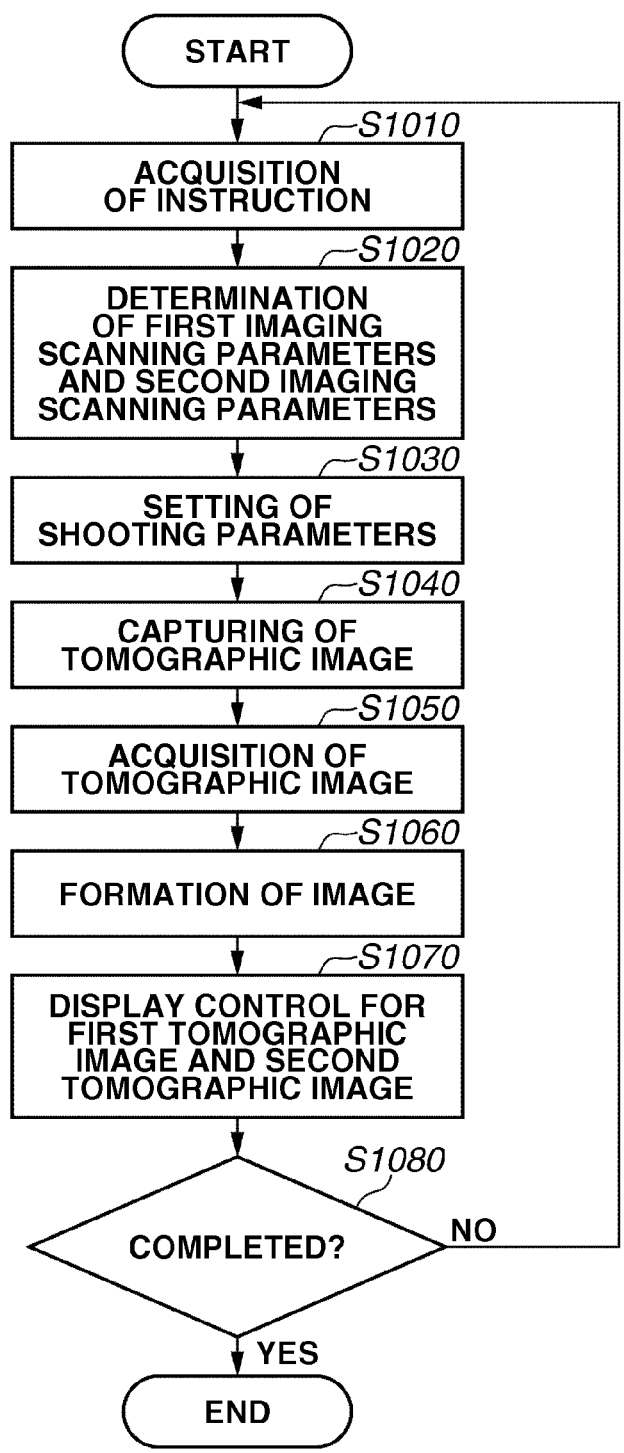
FIG. 10 is a flowchart illustrating a flow of processing that can be performed by a tomographic imaging system according to another exemplary embodiment of the present invention.

Further, the image processing apparatus 110 performs processing similar to that described in the fourth exemplary embodiment (see FIG. 10). Therefore, the description of the similar processing is not repeated. However, the image processing apparatus 110 according to the present exemplary embodiment performs the following processing in step S1070.

In step S1070, the display control unit 105 performs display control for the three first tomographic images, the three second tomographic images, and the composite second tomographic image, which have been formed in step S1060.

In the display control for the above-described tomographic images, the display control unit 105 performs at least one of the following display controls to indicate the signal light whose shooting parameters are currently adjusted.

(a) The display control unit 105 enlarges the first tomographic image corresponding to the signal light to be adjusted.

(b) The display control unit 105 locates the first tomographic image corresponding to the signal light to be adjusted at a position adjacent to the second tomographic image.

(c) The display control unit 105 positions the first tomographic image corresponding to the signal light to be adjusted on the foreside of the display screen.

(d) The display control unit 105 changes the color or the shape of the frame of the first tomographic image corresponding to the signal light to be adjusted.

The display control according to the present invention is not limited to the above-described example. Any other display control capable of emphasizing the first tomographic image corresponding to the signal light to be adjusted is employable.

Figure 14A:
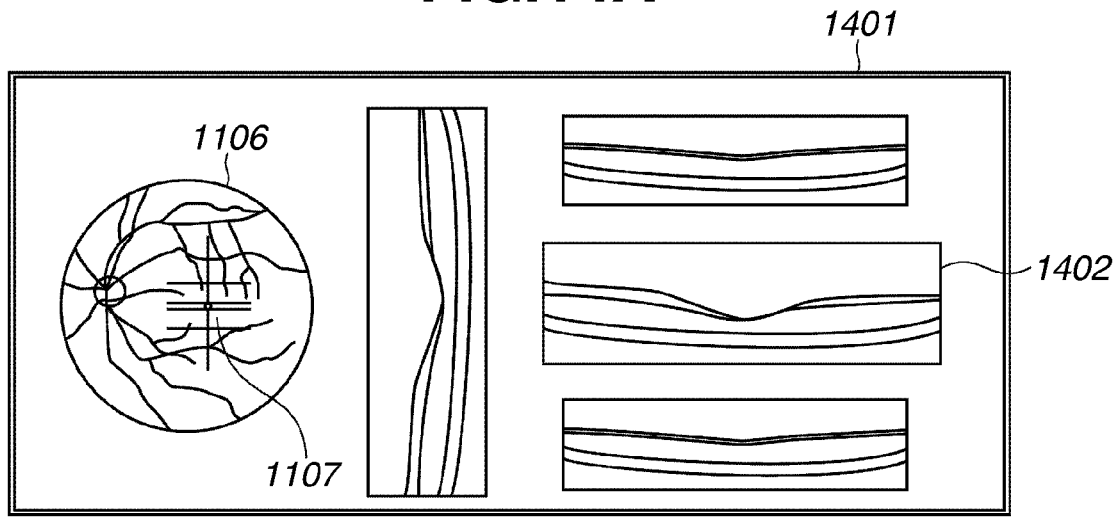
FIG. 14A illustrates another display screen that can be displayed by the display control unit according to an exemplary embodiment of the present invention.
Figure 14B:
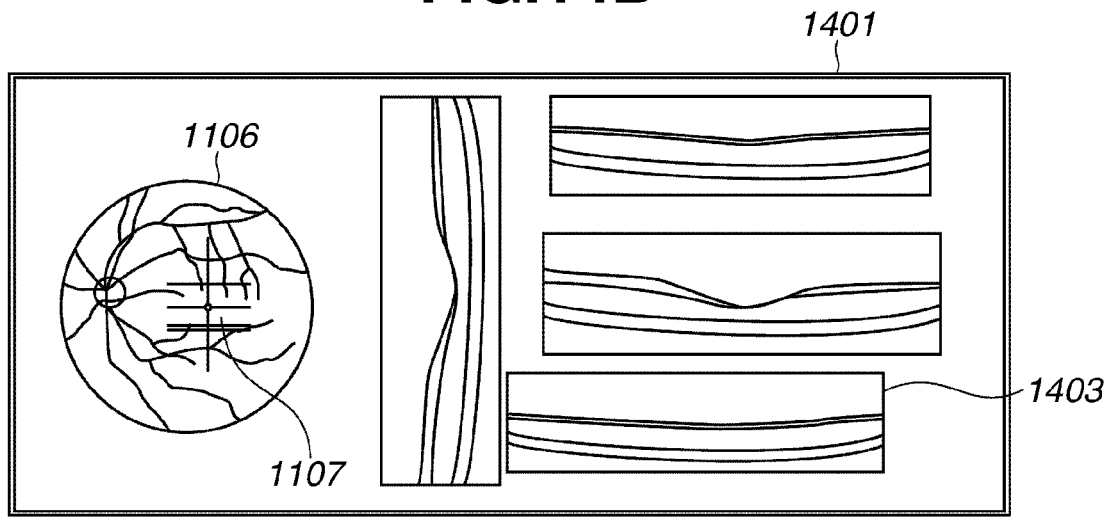
FIG. 14B illustrates another display screen that can be displayed by the display control unit according to an exemplary embodiment of the present invention.

FIGS. 14A to 14D illustrate display examples that can be displayed on the display apparatus 130 by the image processing apparatus 110 according to the present exemplary embodiment. FIG. 14A illustrates a first tomographic image 1402 that has been enlarged because the signal light corresponding to the first tomographic image 1402 is a target to be adjusted. FIG. 14B illustrates a first tomographic image 1403 that is positioned adjacent to the display position of the second tomographic image because the signal light corresponding to the first tomographic image 1403 is a target to be adjusted.

Figure 14C:
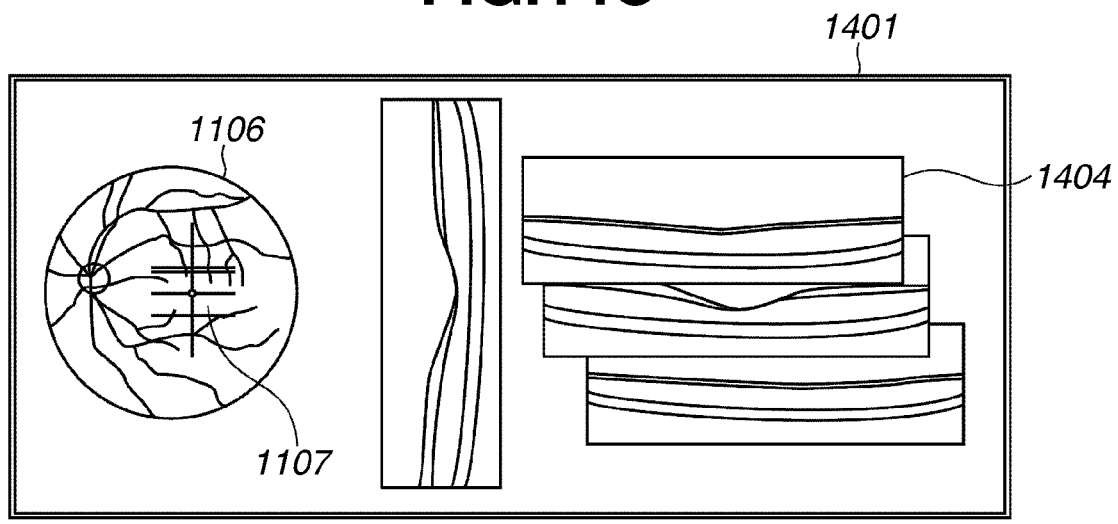
FIG. 14C illustrates another display screen that can be displayed by the display control unit according to an exemplary embodiment of the present invention.
Figure 14D:
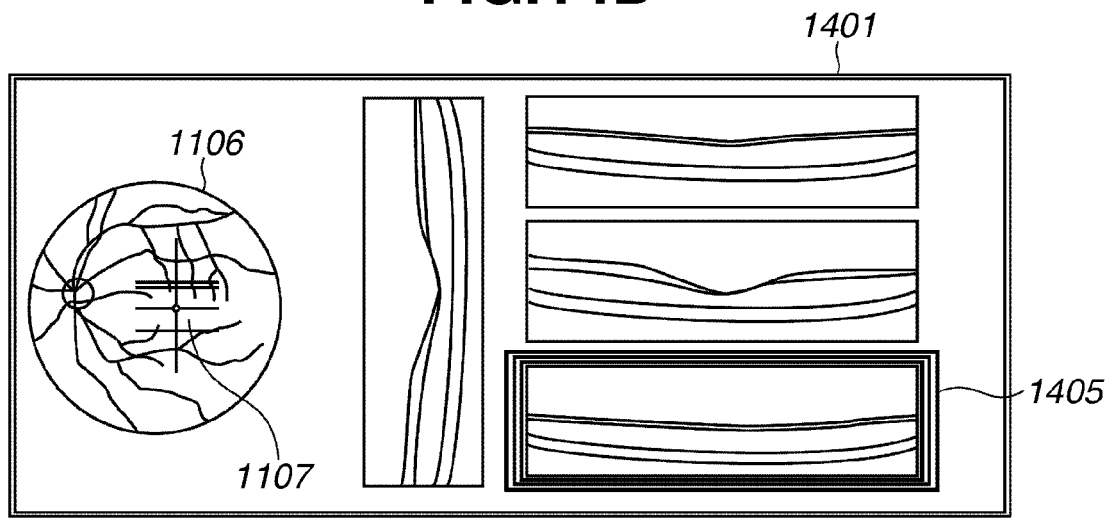
FIG. 14D illustrates another display screen that can be displayed by the display control unit according to an exemplary embodiment of the present invention.

Further, FIG. 14C illustrates a first tomographic image 1404 that is positioned on the foreside of the display screen because the signal light corresponding to the first tomographic image 1404 is a target to be adjusted. FIG. 14D illustrates a first tomographic image 1405 that has an emphasized frame shape because the signal light corresponding to the first tomographic image 1405 is a target to be adjusted.

As described above, performing the display control for explicitly indicating the first tomographic image that corresponds to the signal light be adjusted enables users to easily recognize the signal light to be adjusted.

In the above-described exemplary embodiments, the image acquisition unit 101 acquires the fundus image captured by the fundus camera together with the OCT tomographic images. However, the fundus image is not limited to the image captured by the fundus camera. For example, an image captured by a scanning laser ophthalmoscopy (SLO) (confocal) is usable.

In the above-described exemplary embodiments, an electric circuit that constitutes each functional block in the image processing apparatus or in the optical coherence tomographic imaging system can realize the present invention. However, the present invention is not limited to the above-described exemplary embodiments. For example, the image processing apparatus can be replaced by a system including a plurality of apparatuses that cooperatively perform the above-described processing. Further, each functional block can be replaced by a plurality of circuits or devices that cooperatively perform comparable processing.

Moreover, to realize the present invention, it may be useful to provide an optical coherence tomographic imaging apparatus that has functions comparable to the image processing apparatus and the display apparatus described in the above-described exemplary embodiments.

Further, to realize the present invention, a storage medium storing software program code for realizing the functions of the above-described exemplary embodiments can be supplied to a system or an apparatus. A computer (or CPU or microprocessing unit (MPU)) provided in the system or the apparatus can execute the program code stored in the storage medium.

Further, when the computer executes the readout program code, an operating system (OS) running on the computer performs a part or the whole of actual processing so as to realize the functions of the above-described exemplary embodiments. It is also useful that a computer includes two or more CPUs. In this case, a plurality of CPUs can cooperatively perform processing so as to realize the present invention.

Further, in this case, the program code itself read out of the storage medium realizes the functions of the above-described exemplary embodiments. The program or the storage medium storing the program code constitutes the present invention.

Further, the program code read out of the storage medium can be written into a memory of a function expansion card or into a memory of a function expansion unit, which are attachable to a computer. In this case, an arithmetic apparatus provided in the function expansion card or the function expansion unit can execute a part or the whole of the actual processing so as to realize the functions of the above-described exemplary embodiments. In this case, the present invention can be realized by the functions of a circuit constituting a hardware configuration and cooperation between software and hardware configurations.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Applications No. 2010-082811 filed Mar. 31, 2010 and No. 2011-032218 filed Feb. 17, 2011, which are hereby incorporated by reference herein in their entirety.

The invention claimed is:

1. A display control apparatus for displaying an optical coherence tomographic (OCT) image captured at a coherence gate position, the display control apparatus comprising:
an image acquisition unit configured to respectively acquire a first, second, third and fourth OCT tomographic images at first, second, third and fourth cross sections, the first cross section and the second cross section facing each other, the first cross section and the third cross section facing each other, the fourth cross section intersecting with the first, second and the third cross sections;
a layout determination unit configured to determine a layout of the first, second, third and fourth OCT tomographic images such that the first, second, third and fourth OCT tomographic images are arranged in an arrangement corresponding to an arrangement of the first, second, third and fourth cross sections; and
a display control unit configured to display, with information for adjusting the coherence gate position on a display screen, the first, second, third and fourth OCT tomographic images in the layout determined by the layout determination unit.

2. The display control apparatus according to claim 1, wherein the image acquisition unit is configured to acquire OCT tomographic images captured at the second and third cross sections that are substantially parallel to one another.

3. The display control apparatus according to claim 1, further comprising:
a selection unit configured to select at least one OCT tomographic image from among the first, second, and third OCT tomographic images; and
a status determination unit configured to determine display statuses of the first, second, and third OCT tomographic images,
wherein the status determination unit is configured to determine a display status of the at least one OCT tomographic image selected by the selection unit to be a display status larger than those of the other tomographic images.

4. The display control apparatus according to claim 1, further comprising an adjustment unit configured to adjust the coherence gate position about at least one of the first, second, and third OCT tomographic images,
wherein the display control unit is configured to display, on the display screen, the OCT tomographic image with the coherence gate position which has been changed according to adjustment by the adjustment unit.

5. The display control apparatus according to claim 1, wherein the image acquisition unit is configured to acquire a plurality of OCT tomographic images of a target to be captured along a plurality of main scanning lines that are different in direction,
wherein the display control unit is configured to display the plurality of OCT tomographic images on the display screen using a layout that can express differences in the direction of each main scanning line so as to reflect a relative relationship between respective main scanning line directions with respect to the target to be captured in respective OCT tomographic images, and
wherein the display control unit is configured to display, on at least one tomographic image of the plurality of OCT tomographic images, a position corresponding to another tomographic image of the plurality of OCT tomographic images.

6. The display control apparatus according to claim 5, wherein the layout determination unit is configured to determine a layout of the acquired plurality of tomographic images in such a way as to retain the relative relationship between respective scanning line directions at a position corresponding to a target to be captured.

7. The display control apparatus according to claim 6, wherein the layout determination unit is configured to determine a layout of one of the tomographic images and to determine a layout of the other of the tomographic images based on the determined layout of the one of the tomographic images and information indicating the relative relationship.

8. The display control apparatus according to claim 6, wherein the image acquisition unit is configured to acquire a first tomographic image that can be obtained while scanning a target to be captured in a first direction with signal light that reaches the target to be captured and a second tomographic image that can be obtained while scanning the target to be captured in a second direction perpendicular to the first direction with the signal light, and
wherein the layout determination unit is configured to determine a layout of the first tomographic image and the second tomographic image so that the first direction in the first tomographic image becomes perpendicular to the second direction in the second tomographic image.

9. The display control apparatus according to claim 1, wherein the display control unit is configured to display, on the display screen, an intersecting position on at least one of the tomographic images if a plurality of cross sections of a target to be captured, which include respective tomographic images, intersect each other.

10. The display control apparatus according to claim 1, wherein a target to be captured is a retina, wherein the image acquisition unit is configured to acquire a fundus image including B-scan positions that correspond to the plurality of tomographic images, and wherein the display control unit is configured to display the acquired fundus image.

11. The display control apparatus according to claim 10, wherein the display control unit is configured to display the plurality of tomographic images in association with the B-scan positions displayed in the fundus image.

12. The display control apparatus according to claim 11, wherein the layout determination unit is configured to determine a layout of the fundus image or the tomographic images in such a way as to set B-scan directions displayed on the fundus image to be parallel to B-scan directions on the tomographic images.

13. The display control apparatus according to claim 11, wherein the layout determination unit is configured to determine a layout of a tomographic image captured along a B-scan direction parallel to a B-scan direction in a final shooting operation, among the plurality of tomographic images, in such a way as to set the B-scan direction of the tomographic image to be parallel to the horizontal direction of the display screen.

14. The display control apparatus according to claim 10, further comprising a selection unit configured to select either the tomographic images or the fundus image displayed by the display control unit, and wherein the display control unit is configured to display, on the display screen, either the tomographic images or the fundus image based on a selection by the selection unit.

15. The display control apparatus according claim 1, further comprising:

an adjustment unit configured to adjust a shooting condition used when a tomographic imaging apparatus captures the tomographic image of a target to be captured, wherein the display control unit is configured to display, on the display screen, tomographic images that correspond to the shooting condition adjusted by the adjustment unit; and a transmission unit configured to transmit a re-shooting instruction to the tomographic imaging apparatus.

16. The display control apparatus according to claim 15, wherein the display control unit is configured to display, on at least one of the plurality of tomographic images, the coherence gate position of the tomographic image to be captured in response to the instruction received from the transmission unit.

17. The display control apparatus according to claim 1, wherein the image acquisition unit is configured to acquire a plurality of tomographic images obtained using respective signal light beams, which can be captured by an optical coherence tomographic imaging apparatus that can simultaneously scan a plurality of positions of a target to be captured with a plurality of signal light beams, and wherein the display control unit is configured to display the coherence gate position for each of the acquired plurality of tomographic images.

18. The display control apparatus according to claim 1, wherein the display control unit is configured to display, on the display screen, an intersecting position on at least one of the tomographic images which intersects with one of the tomographic images.

19. The display control apparatus according to claim 18, further comprising an intersection determination unit configured to determine whether two of the tomographic images are intersectional.

20. A display control method for displaying an optical coherence tomographic (OCT) image captured at a coherence gate position, the method comprising:

respectively acquiring first, second, third and fourth OCT tomographic images respectively captured at first, second, third and fourth cross sections the first cross section and the second cross section facing each other, the first cross section and the third cross section facing each other, and the fourth cross section intersecting with the first, second and third cross sections;

determining a layout of the first, second, third and fourth OCT tomographic images such that the first, second, third and fourth OCT tomographic images are arranged in an arrangement corresponding to an arrangement of the first, second, third and fourth cross sections; and displaying, with information for adjusting the coherence gate position on a display screen, the first, second, third and fourth OCT tomographic images in the determined layout.

21. The display control apparatus according to claim 1, wherein the information for adjusting the coherence gate position is indicia which represents the coherence gate position superimposing on a display of a coherence gate adjustable range.

* * * * *